US009938584B2

(12) United States Patent
Detmer et al.

(10) Patent No.: US 9,938,584 B2
(45) Date of Patent: Apr. 10, 2018

(54) OLIGONUCLEOTIDES AND METHODS FOR DETECTING KRAS AND PIK3CA MUTATIONS

(71) Applicant: Siemens Healthcare Diagnostics Inc., Tarrytown, NY (US)

(72) Inventors: Jill Detmer, Kensington, CA (US); Arejas J. Uzgiris, Berkeley, CA (US); Andy Ying, Fremont, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/420,244

(22) Filed: Jan. 31, 2017

(65) Prior Publication Data
US 2017/0137894 A1 May 18, 2017

Related U.S. Application Data

(62) Division of application No. 14/568,208, filed on Dec. 12, 2014, now Pat. No. 9,605,321, which is a division of application No. 13/521,595, filed as application No. PCT/US2011/020098 on Jan. 4, 2011, now Pat. No. 8,940,486.

(60) Provisional application No. 61/294,123, filed on Jan. 12, 2010.

(51) Int. Cl.
*C12Q 1/68* (2006.01)
(52) U.S. Cl.
CPC ..... *C12Q 1/6886* (2013.01); *C12Q 2600/106* (2013.01); *C12Q 2600/156* (2013.01); *C12Q 2600/16* (2013.01)
(58) Field of Classification Search
None
See application file for complete search history.

(56) References Cited

U.S. PATENT DOCUMENTS

| 6,103,476 | A | 8/2000 | Tyagi | |
|---|---|---|---|---|
| 2005/0272083 | A1 | 12/2005 | Seshagiri | |
| 2007/0224208 | A1* | 9/2007 | Guo | A61K 39/0011 424/184.1 |
| 2008/0305478 | A1* | 12/2008 | Chun | C12Q 1/6848 435/6.11 |
| 2009/0280486 | A1 | 11/2009 | Chun | |

FOREIGN PATENT DOCUMENTS

| CN | 101445832 | 6/2009 |
|---|---|---|
| WO | 2006/095981 | 9/2006 |
| WO | 2008151031 | 12/2008 |
| WO | 2009040557 | 4/2009 |
| WO | 2012095505 | 7/2012 |

OTHER PUBLICATIONS

Dotsch et al. "Quantitative TaqMan Real-Time PCR: Diagnostic and Scientific Applications", in: Walker et al., Medical Biomethods Handbook (New Jersey, Humana Press, 2005), pp. 305-313.*
Schildkraut et al. (1965) Dependence of the Melting Temperature of DNA on Salt Concentration. Biopolymers, 3:195-208.*
Package Insert: Therascreen KRAS mutation test kit: for the detection of 7 mutations in the KRAS gene. DxS (Diagnostic Innovations): (May 2009).
Package Insert: Therascreen PIK3CA mutation test kit: For the detection of 4 mutations in exons 9 and 20 of the PIK3CA gena DxS (Diagnostic Innovations) (Jul. 2009).
Amado et al., Wild-type KRAS is Required for Panitumumab Efficiency in Patients with Metastatic Colorectal Cancer, J. Clin Oncol 26(10):1626-1634 (2008).
Baker et al., Evaluation of Tumor Gene Expression and KRAS Mutations in FFPE Tumor Tissue as Predictors of Response to Cetuximab in Metastatic Colorectal Cancer, J Clin Oncol 26(15S): May 20 Supplement, Abstract 3512 (2008).
Clayton, S.J., KRAS Point Mutation Detection in Lung Cancer: Comparison oOf Two Approaches to Somatic Mutation Detection Using ARMS Allele-Specific Amplification, Clin Chem 46(12):1929-1938 (2000).
Gormally, et al., TP53 and KRAS2 Mutations in Plasma DNA of Healthy Subjects and Subsequent Cancer Occurrence: A Prospective Study, Cancer Res 66(13):6871-6876 (2006).
Karakas, et al., Mutation of the PIK3CA Oncogene in Human Cancers, British J Cancer 94(4):455-459 (2006); Li et al., Mutations of PIK3CA in Gastric Adenocarcinoma, Biomed Central Cancer 5:29 (2005); Qiu et al., PIK3CA Mutations in Head and Neck Squamous Cell Carcinoma, Clin Cancer Res. 12(5):1441-1446 (2006).
Krypuy et al., High Resolution Melting Analysis for the Rapid and Sensitive Detection of Mutation in Clinical Samples: KRAS Codon 12 and 13 Mutations in Non-Small Cell Lung Cancer, BCM Cancer 6:295 (2006).
Li et al., Mutations of PIK3CA in Gastric Adenocarcinoma, BMC Cancer 5:29 (2005).
Massarelli et al., KRAS Mutation is an Important Predictor of Resistance to Therapy with Epidermal Growth Factor Receptor Tyrosine Kinase Inhibitors in Non-Small Cell Lung Cancer, Clin Cancer Res. 13(10):2890-2896 (2007).
Sartore-Bianchi et al., PIK3CA Mutations in Colorectal Cancer are Associated with Clinical Resistance to EGFR-Targeted Monoclonal Antibodies, Cancer Res. 69(5):1851-1857 (2009).
Van Cutsem et al., KRAS Status and Efficacy in the First-Line Treatment of Patients with Metastatic Colorectal Cancer (mCRC) Treated with FOLFIRI with or without Cetuximab: The CRYSTAL Experience, J Clin Oncol 26(15S): May 20 Supplement, Abstract 2 (2008).

(Continued)

Primary Examiner — Neil P Hammell

(57) ABSTRACT

Provided are oligonucleotides that are capable of detecting KRAS and PIK3CA mutations in both cancer patients and healthy individuals with high specificity in kPCR assays. When the oligonucleotides are used as forward primers in conjunction with a defined genotyping algorithm spreadsheet, the primers are capable of enhancing detection of KRAS codon 12, 13, and 61 and PIK3CA codon 542, 545, and 1047 single nucleotide polymorphisms (SNPs) in a background of wild-type sequences. The oligonucleotides of the present invention are also capable of preventing pseudogene amplification when the oligonucleotides are hybridized as reverse primers or detection probes to the mismatch sequences.

11 Claims, 11 Drawing Sheets

(56) References Cited

OTHER PUBLICATIONS

Van Zakowski et al., Reflex Testing of Lung Adenocarcinomas for EGFR and KRAS Mutations: The Memorial Sloan-Kettering Experience, J. Clin Oncol 26(15S): May 20 Supplement, Abstract 22031 (2008).
Qiu et al., PIK3CA Mutations in Head and Neck Squamous Cell Carcinoma, Clin Cancer Res. 12(5):1441-1446 (2006).
International Search Report for PCT/US11/020098 dated May 19, 2011.
Khanna, et al., Multiplex PCR/LDR for Detection of K-ras Mutations in Primary Colon Tumors, Oncogene,18(1): 27-38 (1999).
Dahse, R. et al.; KRAS status and epidermal growth factor receptor expression al determinants for anti-EGFR therapies in salivary gland carcinomas; Oral Oncology, 45(9): 826-829, (2009).
Chun, J. et al.; Dual priming oligonucleotide system for the multiplex detection of respiratory viruses and SNP genotyping of CYP2C19 gene; Nucleic Acids Research; 35(6); e40, (2007).
*Homo Sapiens* Chromosome 3, NCBI Reference Assembly, Complete Sequence, NC_000003.10, GI:89161205, priority to Mar. 3, 2008, 2 pages.
*Homo Sapiens* Chromosome 22, Alternate Assembly (Based on HuRef), Whole Genome Shotgun Sequence, AC_000154, GI:157729478, Priority to Mar. 3, 2008, 2 pages.
Kwok, P., Methods for Genotyping Single Nucleotide Polymorphisms, Annual Review of Geomics and Human Genetics, 2:235-58, (2001).
Rozen et al., Primer3 on the WWW for General Users and for Biologist Programmers, Methods in Molecular Biology. pp. 365-389, (2000).
Aquino de Muro, Marilena, Probe Design, Production, and Applications, Medical Biomethods Handbook, pp. 13-23, (2005).
Tanaka et al., Absence of PIK3CA Hotspot Mutations in Hepatocellular Carcinoma in Japanese Patients, Oncogenomics, 25:2950-2952, (2006).
Board et al., Multiplexed Assays for Detection of Mutations in PIK3CA, Clinical Chemistry, 54(4):757-760 (2008).
Miyake et al., PIK3CA Gene Mutations and Amplifications in Uterine Cancers, Identified by Methods that Avoid confounding by PIK3CA Pseudogne Sequence,Science Direct, Cancer Letters 261: 120-126, (2008).
Garcia-Rostan et al., Mutation of the PIK3CA Gene in Anaplastic Thyroid Cancer, Cancer Research, 65:10199-10207, (2005).
Schildkraut et al., Dependence of the Melting Temperature of DNA on Salt Concentration, Biopolymers, 3:195-208, (1965).
Board et al., Multiplexed Assays for Detection of Mutations in PIK3CA, Clinical Chemistry, 54(4): 757-760.
Samuels, Yardena et al; "High frequency of mutations of the PIK3CA gene in Human cancers"; Science American association for the advancement of science; vol. 304; No. 5670; pp. 554; (2004).
Kawano, Osamu et al; "PIK3CA mutation status in Japanese lung cancer patients"; Lung cancer; Elsevier; Amsterdam; vol. 54; No. 2; pp. 209-215; (2006).
Board, Ruth et al; "Multiplexed assays for detection of mutations in PIK3CA"; Clinical chemis; American association for clinical chemistry; vol. 54; No. 4; pp. 757-760; (2008).

\* cited by examiner

KRAS(EXON2) OLIGONUCLEOTIDE MAP
(SEQ ID NO. 34)

TCCTTTGAGAGCCTTTAGCCGCCGCAGAACAGCAGTCTGGCTATTTAGATAGAAC
AACTTGATTTTAAGATAAAAGAACTGTCTATGTAGCATTTATGCATTTTTCTTAA
GCGTCGATGGAGGAGTTTGTAAATGAAGTACAGTTCATTACGATACACGTCTGCA
GTCAACTGGAATTTTCATGATTGAATTTTGTAAGGTATTTTGAAATAATTTTTCA
TATAAAGGTGAGTTTGTATTAAAAGGTACTGGTGGAGTATTTGATAGTGTATTAA
CCTTATGTGTGACATGTTCTAATATAGTCACATTTTCATTATTTTTATTATAAGG
CCTGCTGAAAATGACTGAATATAAACTTGTGGTAGTTGGAGCTGGTGGCGTAGGC
AAGAGTGCCTTGACGATACAGCTAATTCAGAATCATTTTGTGGACGAATATGATC
CAACAATAGAGGTAAATCTTGTTTTAATATGCATATTACTGGTGCAGGACCATTC
TTTGATACAGATAAAGGTTTCTCTGACCATTTTCATGAGTACTTATTACAAGATA
ATTATGCTGAAAGTTAAGTTATCTGAAATGTACCTTGGGTTTCAAGTTATATG

KRAS CODON 12 AND 13 SEQUENCES

| No. | Sequence | Map Locn | Sequence 5' to 3' | Strand |
|---|---|---|---|---|
| 1 | KRAS12 WT GGT | 18157292-18157258 | ATGACTGAATATAAACTTGTGGTAGTTGGAGCTGG (SEQ ID NO. 1) | - |
| 2 | KRAS12 Mut AGT | 18157292-18157259 | ATGACTGAATATAAACTTGTGGTAGTTGGAGCTA (SEQ ID NO. 2) | - |
| 3 | KRAS12 Mut CGT | 18157292-18157259 | ATGACTGAATATAAACTTGTGGTAGTTGGAGCTC (SEQ ID NO. 3) | - |
| 4 | KRAS12 Mut TGT | 18157292-18157259 | ATGACTGAATATAAACTTGTGGTAGTTGGAGCTT (SEQ ID NO. 4) | - |
| 5 | KRAS12 Mut GAT | 18157292-18157258 | ATGACTGAATATAAACTTGTGGTAGTTGGAGTTGA (SEQ ID NO. 5) | - |
| 6 | KRAS12 Mut GCT | 18157292-18157258 | ATGACTGAATATAAACTTGTGGTAGTTGGAGTTGC (SEQ ID NO. 6) | - |
| 7 | KRAS12 Mut GTT1 | 18157292-18157258 | ATGACTGAATATAAACTTGTGGTAGTTGGAGTTGT (SEQ ID NO. 7) | - |
| 8 | KRAS12 Mut GTT2 | 18157292-18157258 | ATGACTGAATATAAACTTGTGGTAGTTGGAGCTGT (SEQ ID NO. 8) | - |
| 9 | KRAS13 Mut GAC | 18157287-18157255 | TGAATATAAACTTGTGGTAGTTGGAGTTGATTTTGA (SEQ ID NO. 9) | - |
| 10 | KX2P (probe) | 18157248-18157220 | CAAGAGTGCCTTGACGATACAGCTAATTC (SEQ ID NO. 10) | - |
| 11 | KRAS rev primer | 18157130-18157154 | GTATCAAAGAATGGTCCTGCACCAG (SEQ ID NO. 11) | + |
| 12 | KX2F fwd primer | 18157292-18157265 | ATGACTGAATATAAACTTGTGGTAGTTG (SEQ ID NO. 12) | - |

| KRAS CODON 61 SEQUENCES |||||
|---|---|---|---|---|
| No. | Sequence | Map Locn | Sequence 5' to 3' | Strand |
| 13 | KRAS61 WT CAA | 18140409- 18140437 | TCTCTTGGATATTCTCGACACATTTTTCA (SEQ ID NO. 23) | − |
| 14 | KRAS61 Mut CTA | 18140409- 18140437 | TCTCTTGGATATTCTCGACACATTTTTCT (SEQ ID NO. 24) | − |
| 15 | KRAS61 rev_prmr | 18140282- 18140304 | TTTAAACCCACCTATAATGGTGAA (SEQ ID NO. 25) | + |
| 16 | KRAS61 probe | 18140373- 18140394 | AGTACAGTGCAATGAGGGACCA (SEQ ID NO. 26) | − |

FIG. 2B

KRAS CODON 61 MAP

| Map Location | Sequence 5' to 3' |
|---|---|
| 18140578-18140519 | CCTTTGCCCATTTTTAAATTGAATTTTTTGTGTTGAGTTGTATATAACACCTTTTTTGA (Seq ID No. 27) |
| 18140518-18140459 | AGTAAAAGGTGCACTGTAATAATCCAGACTGTGTTTCTCCCTTCTCAGGATTCCTACAGG (Seq ID No. 28) |
| 18140458-18140399 | AAGCAAGTAGTAATTGATGGAGAAACCTGTCTCTTCTTGGATATTCTCGACACAGCAGGTCAA (Seq ID No. 29) |
| 18140398-18140339 | GAGGAGTACAGTGCAATGAGGGACCAGTACACATGAGGACTGGGGAGGGCTTTCTTTGTGTA (Seq ID No. 30) |
| 18140338-18140279 | TTTGCCATAAATAATACTAAATCATTTGAAGATATTCACCATTATAGGTGGGTTTAAATT (Seq ID No. 31) |
| 18140278-18140219 | GAATATAATAAGCTGACACATTAAGGAGTAATTATAGTTTTTATTTTTTGAGTCTTTGCTAA (Seq ID No. 32) |
| 18140218-18140159 | TGCCATGCATATAATATTTAATAAAAATTTTTAAATAATGTTTATGAGGTAGGTAATATC (Seq ID No. 33) |

FIG. 2C

PI3KCA (CHROMOSOME 3) OLIGONUCLEOTIDE MAP

PIK3CA EXON 9
(SEQ ID NO. 35)

ACAGCTCAAAGCAATTTCTACACGAGATCCTCTCTCTGAAATCACTGAGCAGGAG

AAAGATTTTCTATGGAGTCACAGgtaagtgctaaaatggagattctctgtttctt tttctttattacagaaaaaataactgaatttggctgatctcagcatgttttacc atacctattggaataaataagcagaatttacatg

PIK3CA EXON 20
(SEQ ID NO. 36)

CAGAACTACAATCTTTTGATGACATTGCATACATTCGAAAGACCCTAGCCTTAGA

TAAAACTGAGCAAGAGGCTTTGGAGTATTTCATGAAACAAATGAATGATGCACAT

CATGGTGGCTGGACAACAAAAATGGATTGGATCTTCCACACAATTAAACAGCATG

CATTGAACTGAAAAGATAACTGAGAAAATGAAAGCTCACTCTGGAATTCCACACT

GCACTGT

FIG. 7

PIK2CA EXON 9 AND 20 SEQUENCES

| No. | Sequence Name | Sequence 5' to 3' | |
|---|---|---|---|
| 1 | Ex9Wt_Na.Seq | TCTCTCTGAAATCACTGAGCA | (SEQ ID NO. 13) |
| 2 | 542_Mu1 (E542K) | AAAGCAATTTCTACACGAGATCCTTTTTCTA | (SEQ ID NO. 14) |
| 3 | 545_Mu1 (E545K) | TACACGAGATCCTCTCTCTGATTTTTCTA | (SEQ ID NO. 15) |
| 4 | 545_Mu2 (E545D) | TACACGAGATCCTCTCTCTGAAATTTTTGAT | (SEQ ID NO. 16) |
| 5 | Ex9_RevPrimer2 | CATGCTGAGATCAGCCAAAT | (SEQ ID NO. 17) |
| 6 | Ex9_ProbeE | AGTCACAGGTAAGTGCTAAAATGGAGATTCT | (SEQ ID NO. 18) |
| 7 | Ex20_Na.Seq.Fwdpr | TTGGAGTATTTCATGAAACAAATGAAT | (SEQ ID NO. 19) |
| 8 | 1047_Mut1 (H1047R) | TTGGAGTATTTCATGAAACAAATGAATTTTTTACG | (SEQ ID NO. 20) |
| 9 | Ex20_RevPrimer1 | TGGAATCCAGAGTGAGCT | (SEQ ID NO. 21) |
| 10 | Ex20_ProbeA | TGGTGGCTGGACAACAAAAATGGAT | (SEQ ID NO. 22) |

FIG. 8

CHROMOSOME 3 (SEQ ID NO: 38) AND CHROMOSOME 22 (SEQ ID NO: 37) SEQUENCE ALIGNMENT

```
Chr22   529  AAGTTTATTGAAAATGTATTTGCTTTTTTTGTAAATCATCTGTGAATCCA    578
Chr03   901  adattattgaaaatgtatttgcttttttctgtaaatcatctgtgaatcca    950

Chr22   579  GAGGGGAAAAATATGACAAGAAAAGCTATATAAGATATTATTTTATTTTA    628
Chr03   951  gaggggaaaaatatgacaagaaaagctatataagatattattttatttta   1000

Chr22   629  CAGAGTAACAGACTAGCTAGAGACAATGAATTAAGGGAAAATGACAAAGA    678
Chr03  1001  cagagtaacagactagctagagacaatgaattaagggaaaatgacaaaga   1100

Chr22   679  ACAGCTCAAAGCAATTTCTACACGAGATCCTCTCTGAAATCACTGAGCGC    728   E542K GAA>AAA
Chr03  1051  acagctcaaagcaattctacacgagatcctctctgaaatcactgagtgat   1150   E545K GAG>AAG
                                                                       E545D GAG>GAT Chr22   729  AGGAGAAAGATTTTCTATGGA-CCACAGGTAAGTGCTAAAAATGGAGATTC    777
Chr03  1101  aggagaaagattttctatggatccacaggtaagtgctaaaaatggagattc   1150

Chr22   778  TCTGTTCTTTTTCTTGATTACAGAAAAAAATAACTGACTTTGGCTGATCT    827
Chr03  1151  tctgttctttttcttgattacagaaaaaaataactgacttggctgatct   1200

Chr22   828  CAGCATGTTTTTACCATACCTATTAGAATAAAATGAAGCAGAATTTACATG    877
Chr03  1201  cagcatgtttttaccatacctattggaataaaatcagaatttacatg      1250
```

FIG. 9

SEQUENCE LISTING

<160> NUMBER OF SEQ ID NOS: 39

<210> SEQ ID NO 1
<211> LENGTH: 35
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (28)..(32)
<223> OTHER INFORMATION: Inosine

<400> SEQUENCE: 1
atgactgaat ataaacttgt ggtagttnnn nntgg                               35

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(31)
<223> OTHER INFORMATION: Inosine

<400> SEQUENCE: 2
atgactgaat ataaacttgt ggtagtnnnn ncta                                34

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(31)
<223> OTHER INFORMATION: Inosine

<400> SEQUENCE: 3
atgactgaat ataaacttgt ggtagtnnnn nctc                                34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(31)
<223> OTHER INFORMATION: Inosine

<400> SEQUENCE: 4
atgactgaat ataaacttgt ggtagtnnnn nctt                                34

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)..(32)
<223> OTHER INFORMATION: Inosine

<400> SEQUENCE: 5
atgactgaat ataaacttgt ggtagttnnn nntga                               35
```

```
<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)..(32)
<223> OTHER INFORMATION: Inosine

<400> SEQUENCE: 6
atgactgaat ataaacttgt ggtagttnnn nntgc                                 35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)..(32)
<223> OTHER INFORMATION: Inosine

<400> SEQUENCE: 7
atgactgaat ataaacttgt ggtagttnnn nntgt                                 35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(31)
<223> OTHER INFORMATION: Inosine

<400> SEQUENCE: 8
atgactgaat ataaacttgt ggtagtnnnn nctgt                                 35

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(30)
<223> OTHER INFORMATION: Inosine

<400> SEQUENCE: 9
tgaatataaa cttgtggtag ttggannnnn tga                                   33

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
```

```
caagagtgcc ttgacgatac agctaattc                                      29
```

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gtatcaaaga atggtcctgc accag                                          25
```

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
atgactgaat ataaacttgt ggtagttg                                       28
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
tctctctgaa atcactgagc a                                              21
```

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(28)
<223> OTHER INFORMATION: Inosine

<400> SEQUENCE: 14

```
aaagcaattt ctacacgaga tccnnnnnct a                                   31
```

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(26)
<223> OTHER INFORMATION: Inosine

<400> SEQUENCE: 15

```
tacacgagat cctctctctg annnnncta                                      29
```

<210> SEQ ID NO 16
<211> LENGTH: 31

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(28)
<223> OTHER INFORMATION: Inosine

<400> SEQUENCE: 16
tacacgagat cctctctctg aaannnnnga t                                    31

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catgctgaga tcagccaaat                                                 20

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
agtcacaggt aagtgctaaa atggagattc t                                    31

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttggagtatt tcatgaaaca aatgaat                                         27

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)..(32)
<223> OTHER INFORMATION: Inosine

<400> SEQUENCE: 20
ttggagtatt tcatgaaaca aatgaatnnn nnacg                                35

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 21
tggaatccag agtgagct                                              18

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggtggctgg acaacaaaaa tggat                                      25

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(27)
<223> OTHER INFORMATION: Inosine

<400> SEQUENCE: 23
tctcttggat attctcgaca cannnnntca                                 30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(27)
<223> OTHER INFORMATION: Inosine

<400> SEQUENCE: 24
tctcttggat attctcgaca cannnnntct                                 30

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttaaacccac ctataatggt gaa                                        23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agtacagtgc aatgagggac ca                                         22

<210> SEQ ID NO 27

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctttgccca tttttaaatt gaattttttg ttgttgagtt gtatataaca ccttttttga      60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agtaaaaggt gcactgtaat aatccagact gtgtttctcc cttctcagga ttcctacagg      60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aagcaagtag taattgatgg agaaacctgt ctcttggata ttctcgacac agcaggtcaa      60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gaggagtaca gtgcaatgag ggaccagtac atgaggactg gggagggctt tctttgtgta      60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tttgccataa ataatactaa atcatttgaa gatattcacc attataggtg ggtttaaatt      60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gaatataata agctgacatt aaggagtaat tatagttttt attttttgag tctttgctaa      60

<210> SEQ ID NO 33
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgccatgcat ataatattta ataaaaattt ttaaataatg tttatgaggt aggtaatatc       60

<210> SEQ ID NO 34
<211> LENGTH: 603
<212> TYPE: DNA
<213> ORGANISM: Homo sapiens

<400> SEQUENCE: 34
tcctttgaga gcctttagcc gccgcagaac agcagtctgg ctatttagat agaacaactt       60
gattttaaga taaagaact gtctatgtag catttatgca ttttttcttaa gcgtcgatgg      120 aggagtttgt aaatgaagta cagttcatta cgatacacgt ctgcagtcaa ctggaattt      180 catgattgaa ttttgtaagg tattttgaaa taattttca tataaaggtg agtttgtatt      240
aaaaggtact ggtggagtat ttgatagtgt attaaccta tgtgtgacat gttctaatat      300
agtcacattt tcattatttt tattataagg cctgctgaaa atgactgaat ataaacttgt      360
ggtagttgga gctggtggcg taggcaagag tgccttgacg atacagctaa ttcagaatca      420
ttttgtggac gaatatgatc caacaataga ggtaaatctt gttttaatat gcatattact      480
ggtgcaggac cattctttga tacagataaa ggtttctctg accattttca tgagtactta      540
ttacaagata attatgctga aagttaagtt atctgaaatg taccttgggt ttcaagttat      600
atg                                                                   603

<210> SEQ ID NO 35
<211> LENGTH: 200
<212> TYPE: DNA
<213> ORGANISM: Homo sapiens

<400> SEQUENCE: 35
acagctcaaa gcaatttcta cacgagatcc tctctctgaa atcactgagc aggagaaaga       60
ttttctatgg agtcacaggt aagtgctaaa atggagattc tctgtttctt tttctttatt      120
acagaaaaaa taactgaatt tggctgatct cagcatgttt ttaccatacc tattggaata      180
aataaagcag aatttacatg                                                  200

<210> SEQ ID NO 36
<211> LENGTH: 227
<212> TYPE: DNA
<213> ORGANISM: Homo sapiens

<400> SEQUENCE: 36
cagaactaca atcttttgat gacattgcat acattcgaaa gacccctagcc ttagataaaa       60 ctgagcaaga ggctttggag tatttcatga acaaatgaa tgatgcacat catggtggct      120
ggacaacaaa aatggattgg atcttccaca caattaaaca gcatgcattg aactgaaaag      180
ataactgaga aaatgaaagc tcactctgga attccacact gcactgt                    227

<210> SEQ ID NO 37
<211> LENGTH: 349
<212> TYPE: DNA
<213> ORGANISM: Homo sapiens

<400> SEQUENCE: 37
```

-continued

```
aagtttattg aaaatgtatt tgcttttttt gtaaatcatc tgtgaatcca gagggggaaaa    60 atatgacaaa gaaagctata taagatatta ttttatttta cagagtaaca gactagctag   120
agacaatgaa ttaagggaaa atgacaaaga acagctcaaa gcaatttcta cacgagatcc   180
tctctctgaa atcactgcgc aggagaaaga ttttctatgg accacaggta agtgctaaaa   240
tggagattct ctgtttcttt ttctttatta cagaaaaaat aactgacttt ggctgatctc   300
agcatgtttt taccatacct attagaataa atgaagcaga atttacatg              349
```

<210> SEQ ID NO 38
<211> LENGTH: 350
<212> TYPE: DNA
<213> ORGANISM: Homo sapiens

<400> SEQUENCE: 38

```
aaatttattg aaaatgtatt tgctttttct gtaaatcatc tgtgaatcca gaggggaaaa    60
atatgacaaa gaaagctata taagatatta tttatttta cagagtaaca gactagctag   120
agacaatgaa ttaagggaaa atgacaaaga acagctcaaa gcaatttcta cacgagatcc   180
tctctctgaa atcactgagc aggagaaaga ttttctatgg agtcacaggt aagtgctaaa   240
atggagattc tctgtttctt tttctttatt acagaaaaaa taactgaatt tggctgatct   300
cagcatgttt ttaccatacc tattggaata aataaatcag aatttacatg              350
```

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
atgactgaat ataaacttgt ggtagt                                          26
```

OLIGONUCLEOTIDES AND METHODS FOR DETECTING KRAS AND PIK3CA MUTATIONS

CROSS-REFERENCE TO RELATED APPLICATIONS

This is a divisional application claiming priority from U.S. Ser. No. 14/568,208 filed Dec. 12, 2014 which is a divisional of U.S. Ser. No. 13/521,595 filed Jul. 11, 2012 which is the US National Stage of International Application No. PCT/US2011/020098 filed Jan. 4, 2011 and claims the benefit thereof. The International Application claims the benefit of U.S. Provisional Application No. 61/294,123 filed Jan. 12, 2010. All of the applications are incorporated by reference herein in their entirety.

SEQUENCE LISTING

The instant application contains a Sequence Listing which has been submitted via EFS-Web and is hereby incorporated by reference in its entirety. Said ASCII copy, created on Sep. 4, 2014 is named SL-2009P14771US02_090814.txt, and is 11,544 bytes in size.

TECHNICAL FIELD

The present invention relates generally to oligonucleotides and methods for detecting KRAS and PIK3CA mutations in patient samples. More specifically, the present invention relates to primers and kPCR assays that are capable of detecting KRAS codon 12, 13, and 61 mutations and PIK3CA codon 542, 545, and 1047 mutations with high specificity and sensitivity.

BACKGROUND OF THE INVENTION

Tyrosine kinase inhibitors (TKIs) are a class of anti-cancerous monoclonal antibody drugs that target tumor growth, such as metastasized colorectal cancers (mCRC). TKIs are designed to block receptors and stop the growth signals that fuel the tumor thereby stopping the growth of the cancer cells.

The family of Ras genes encodes small GTPases that are involved in cellular signal transduction. Mutations in Ras genes can permanently activate the genes and cause inappropriate transmission inside the cell in the absence of extracellular signals. Because the signals result in cell growth and division, dysregulated Ras signaling can ultimately lead to oncogenesis and cancer. The Ras genes encode the Ras superfamily of proteins, which includes the KRAS (Kirsten rat sarcoma viral oncogene homolog) protein, which is encoded by the KRAS gene.

KRAS gene mutations are common in pancreatic cancer, lung adenocarcinoma, colorectal cancer, gall bladder cancer, thyroid cancer, and bile duct cancer. The status of KRAS mutations have been reported as predictive markers of tumor response to epidermal growth factor receptor (EGFR) TKI-targeted therapies; accordingly, the mutational status of KRAS can provide important information prior to the prescription of TKI therapy.

The most common KRAS mutations occur in codons 12 and 13 of exon 2. Other more rarely occurring mutations have been seen in codons 59 and 61 of exon 3. KRAS mutations at codons 12, 13, or 61 have been found to cause Ras proteins to remain longer in their active form, resulting in an over-stimulation of the EGFR pathway; consequently, patients with KRAS mutations at codons 12, 13, or 61 do not respond well to TKI therapy. Further, mutations in KRAS codon 12 or 13 have been shown to be strong predictors of patient non-responsiveness to anti-EGFR monoclonal antibody therapies, such as ERBITUX® (cetuximab; ImClone Systems Inc., New York, N.Y., USA) and VECTIBIX® (panitumumab, Amgen, Thousand Oaks, Calif., USA) for the treatment of certain cancerous conditions, including metastatic colorectal cancer (mCRC) and lung cancer. Massarelli et al., *KRAS Mutation is an Important Predictor of Resistance to Therapy with Epidermal Growth Factor Receptor Tyrosine Kinase Inhibitors in Non-Small Cell Lung Cancer*, CLIN CANCER RES. 13(10):2890-2896 (2007); Amado et al., *Wild-type KRAS is Required for Panitumumab Efficiency in Patients with Metastatic Colorectal Cancer*, J. CLIN ONCOL 26(10):1626-1634 (2008); Van Cutsem et al., *KRAS Status and Efficacy in the First-Line Treatment of Patients with Metastatic Colorectal Cancer (mCRC) Treated with FOLFIRI with or without Cetuximab: The CRYSTAL Experience*, J CLIN ONCOL 26(15S): May 20 Supplement, Abstract 2 (2008); Baker et al., *Evaluation of Tumor Gene Expression and KRAS Mutations in FFPE Tumor Tissue as Predictors of Response to Cetuximab in Metastatic Colorectal Cancer*, J CLIN ONCOL 26(15S): May 20 Supplement, Abstract 3512 (2008); Van Zakowski et al., *Reflex Testing of Lung Adenocarcinomas for EGFR and KRAS Mutations: The Memorial Sloan-Kettering Experience*, J. CLIN ONCOL 26(15S): May 20 Supplement, Abstract 22031 (2008).

On Jul. 20, 2009, the FDA updated the labels of ERBITUX® and VECTIBIX® to include the following statements specific to the use of the drugs for mCRC treatment on the "Indications and Use" sections of the respective labels for the drugs:

"Retrospective subset analyses of metastatic or advanced colorectal cancer trials have not shown a treatment benefit for Erbitux in patients whose tumors had KRAS mutations in codon 12 or 13. Use of Erbitux is not recommended for the treatment of colorectal cancer with these mutations [see Clinical Studies (14.2) and Clinical Pharmacology (12.1)]." ERBITUX® label, Indications and Usage (as of Jul. 20, 2009).

"Retrospective subset analyses of metastatic colorectal cancer trials have not shown a treatment benefit for Vectibix in patients whose tumors had KRAS mutations in codon 12 or 13. Use of Vectibix is not recommended for the treatment of colorectal cancer with these mutations [see Clinical Studies (14) and Clinical Pharmacology (12.1)]." VECTIBIX® label, Indications and Usage (as of Jul. 20, 2009).

One currently used method for detecting KRAS codon 12 and 13 mutations is direct sequencing. A major limitation with using direct sequencing is the sensitivity of the assay. The assay is typically run with a small proportion of tumor/normal cells obtained from a patient biopsy. Direct sequencing will detect a minority population only when it is present in a concentration of approximately 15% or greater.

Another method for detecting KRAS codon 12 and 13 mutations is the commercially available THERASCREEN® KRAS Mutation Test Kit (DxS Limited, Manchester, UK). One disadvantage of the THERASCREEN® KRAS Mutation Test Kit method is that the algorithm used to genotype the DNA sample is different for each of the assays and the cycle threshold (Ct) cutoff value for each assay is variable.

In addition to data that supports the fact that patients with mCRC that have KRAS mutations are clinically resistant to therapy with anti-EGFR monoclonal antibodies, there is also data to suggest that mutations that activate PIK3CA (phosphatidyl inositol 3-kinas catalytic subunit) genes are also associated with resistance to anti-EGFR monoclonal antibodies. Sartore-Bianchi et al., *PIK3CA Mutations in Colorectal Cancer are Associated with Clinical Resistance to EGFR-Targeted Monoclonal Antibodies*, CANCER RES. 69(5): 1851-1857 (2009).

The PIK3CA gene encodes for a lipid kinase that together with KRAS regulates signaling pathways downstream of the EGFR. It is not currently known to what extent the occurrence of PIK3CA mutations affect the responsiveness of patients with mCRC, or other cancers, to anti-EGFR monoclonal antibodies; however the literature suggests that the PIK3CA gene is mutated on average in 15% of human cancers over vast range of tissue types. Karakas, et al., *Mutation of the PIK3CA Oncogene in Human Cancers*, BRITISH J CANCER 94(4):455-459 (2006); Li et al., *Mutations of PIK3CA in Gastric Adenocarcinoma*, BIOMED CENTRAL CANCER 5:29 (2005); Qiu et al., *PIK3CA Mutations in Head and Neck Squamous Cell Carcinoma*, CLIN CANCER RES. 12(5):1441-1446 (2006). The most frequent PIK3CA mutations are E542K (Glu524Lys), E545K (Glu545Lys), and E545D (Glu545Asp) mutations in exon 9 and H1047R (His1047Arg) mutations in exon 20.

SUMMARY OF THE INVENTION

The present invention provides oligonucleotides that detect KRAS mutations in codons 12 and 13 of exon 2 and codon 61 of exon 3 and PIK3CA mutations in codons 542 and 545 of exon 9 and codon 1047 of exon 20. The oligonucleotides of the present invention can detect the mutations with high specificity and sensitivity from small sample sizes that may be assayed in kPCR format.

In one aspect of the invention, there is provided a destabilizing oligonucleotide comprising a 5' segment of 15-35 bases in length complementary to a target sequence of a gene; a 3' segment of 3-5 bases in length complementary to a wild-type or mutant sequence of the gene; and a polydeoxyinosine linker of 3-5 bases in length that separates the 5' segment from the 3' segment.

In another aspect of the invention, there is provided an oligonucleotide for detecting KRAS gene mutations, comprising a 5' segment of 15-35 bases in length complementary to a target sequence of the KRAS gene; a 3' segment of 3-5 bases in length complementary to a wild-type or mutant sequence of the KRAS gene at codons 12, 13, or 61; and a polydeoxyinosine linker of 3-5 bases in length that separates the 5' segment from the 3' segment.

In a further aspect of the invention, there is provided an oligonucleotide for detecting PIK3CA gene mutations, comprising a 5' segment of 15-35 bases in length complementary to a target sequence of the PIK3CA gene; a 3' segment of 3-5 bases in length complementary to a wild-type or mutant sequence of the PIK3CA gene at codons 542, 545, or 1047; and a polydeoxyinosine linker 3-5 bases in length that separates the 5' segment from the 3' segment.

In another aspect of the invention, there is provided a method of detecting KRAS mutations at one or more of codons 12, 13, and 61, comprising the steps of: extracting DNA from a biological sample; assaying the DNA via kPCR for KRAS mutations at one or more of codon 12, 13, and 61 with the KRAS oligonucleotide of the present invention as a forward primer, wherein the kPCR assay is run against a background of wild-type DNA; and determining a cycle threshold (Ct) cutoff value for the KRAS mutation by comparing Ct signal differences between the mutant DNA and the wild-type DNA.

In a further aspect of the invention, there is provided a method of detecting PIK3CA mutations at one or more of codons 542, 545, and 1047, comprising the steps of: extracting DNA from a biological sample; assaying the DNA via kPCR for PIK3CA mutations at one or more of codons 542, 545, and 1047 with the PIK3CA oligonucleotide of the present invention as a forward primer, wherein the kPCR assay is run against a background of wild-type DNA; and determining a cycle threshold (Ct) cutoff value for the PIK3CA mutations by comparing signal differences between the mutant DNA and the wild-type DNA.

In another aspect of the invention, there is provided a method of preventing pseudogene amplification in a biological sample, comprising: identifying at least one sequence of interest of a gene; identifying a at least one homolog with less than 100% similarity to the at least one sequence of interest; identifying chromosome locations of the at least one sequence of interest and the at least one homolog, wherein the at least one sequence of interest and the at least one homolog are located on different chromosomes; identifying nucleotide sequence mismatch sites on the at least one sequence of interest and the at least one homolog; hybridizing the destabilizing oligonucleotide of the present invention to the nucleotide sequence mismatch sites on the at least one sequence of interest; and amplifying the at least one sequence of interest, wherein amplicons resulting from the kPCR assay show no homolog amplification.

In a further aspect of the invention, there is provided a kPCR kit for detecting KRAS mutations, comprising kPCR reagent mixes for detection of KRAS mutations at one or more of codons 12, 13, and 61, comprising the KRAS oligonucleotide of the present invention; Taq polymerase; and instructions for use.

In another aspect of the invention, there is provided a kPCR kit for detecting PIK3CA mutations, comprising kPCR reagent mixes for detection of PIK3CA mutations at one or more of codons 542, 545, and 1047, comprising the PIK3CA oligonucleotide of the present invention; Taq polymerase; and instructions for use.

In a further aspect of the invention, there is provided a kPCR kit for detecting if a patient is responsive to anti-EGFR therapy, comprising kPCR reagent mixes for detection of KRAS mutations at one or more of codons 12, 13, and 61 comprising the KRAS oligonucleotide of the present invention; kPCR regent mixes for detection of PIK3CA mutations at one or more of codons 542, 545, and 1047, comprising the PIK3CA oligonucleotide of the present invention; Taq polymerase; and instructions for use.

Additional aspects and embodiments of the invention will be apparent to those of skill in the art upon practice of the invention and are intended to be covered by the appended claims.

BRIEF DESCRIPTION OF THE DRAWINGS

FIG. 1 shows the oligonucleotide map for the KRAS gene, including exon 2. FIG. 1 discloses SEQ ID NO. 34.

FIG. 2A shows KRAS codon 12 and 13 sequences and locations on Accession # NT_009714.16/Hs12_9871. FIG. 2A discloses SEQ ID NOs. 1-12.

FIG. 2B shows KRAS codon 61 sequences and locations on Accession # NT_009714.16/Hs12_9871. FIG. 2B discloses SEQ ID NOs. 23-26.

FIG. 2C shows the location of the KRAS codon 61 primers and probes of the present invention. FIG. 2C discloses SEQ ID NOs. 27-33.

FIG. 7 shows the oligonucleotide map for exons 9 and 20 of the PIK3CA gene on chromosome 3. FIG. 7 discloses SEQ ID NO. 35 (exon 9) and SEQ ID NO. 36 (exon 20).

FIG. 8 shows PIK3CA exon 9 and 20 sequences.

FIG. 9 shows a comparison of the mismatch sites of exon 9 (on chromosome 3) of the PIK3CA gene with sequence segments from chromosome 22. FIG. 9 discloses SEQ ID NO. 37 (chromosome 22) and SEQ ID NO. 38 (chromosome 3).

DETAILED DESCRIPTION OF THE INVENTION

Figure 3:
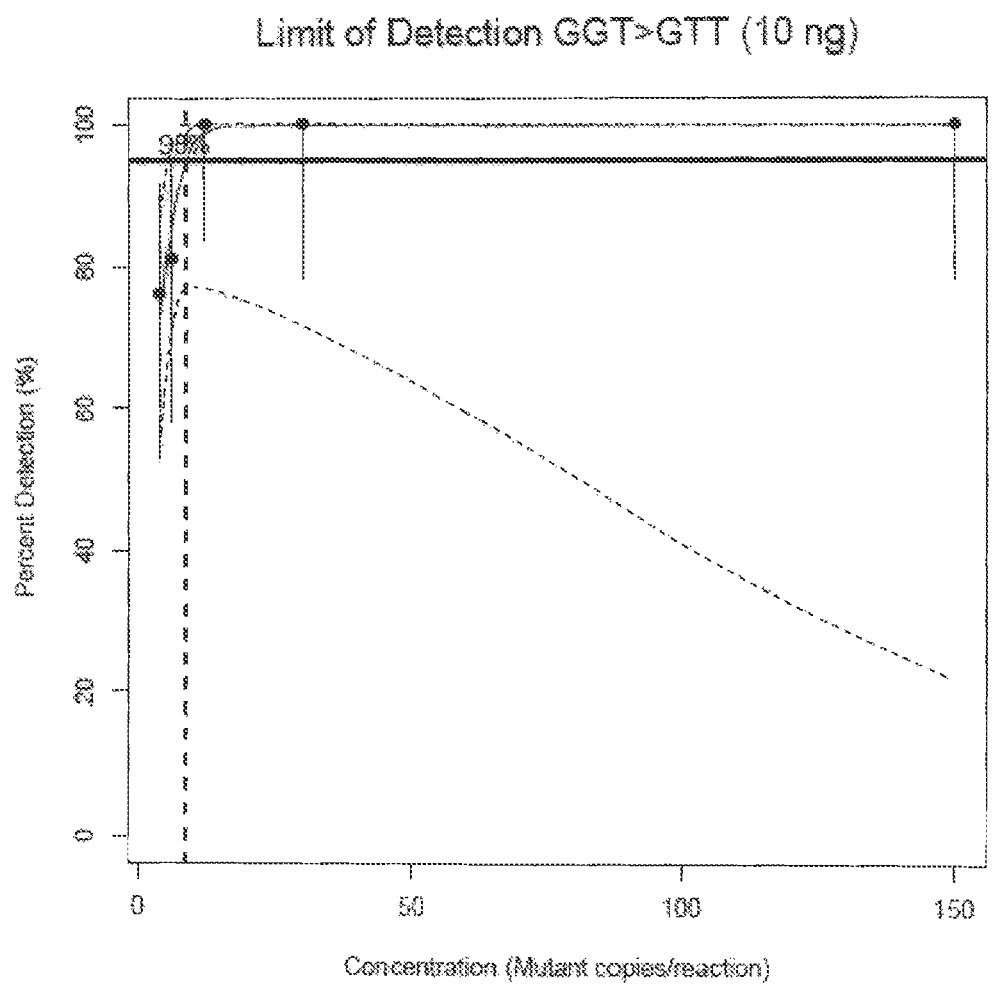
FIGS. 3-6 are limit of detection graphs for four KRAS codon 12 mutations that are analyzed at 10 and 30 ng/μL concentrations.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise.

The terms "kinetic PCR" (kPCR) and "realtime PCR" are used interchangeably herein to refer to the detection of polymerase chain reaction (PCR) products via a fluorescent signal generated by the coupling of a fluorogenic dye molecule and a quencher moiety to the same or different oligonucleotide substrates. Examples of commonly used probes used for kPCR assay include the following probes: TAQMAN® probes, Molecular Beacons probes, SCORPIONS® probes, and SYBR® Green probes. TAQMAN®, Molecular Beacons, and SCORPIONS® probes each have a fluorescent reporter dye (also called a "fluor") attached to the 5' end of the probes and a quencher moiety coupled to the 3' end of the probes. TAQMAN® probes are designed to hybridize to an internal region of a PCR product. In the unhybridized state, the proximity of the fluor and the quench molecules prevents the detection of fluorescent signal from the probe; during PCR, when the polymerase replicates a template on which a TAQMAN® probe is bound, the 5'-nuclease activity of the polymerase cleaves the probe thus, increasing fluorescence with each replication cycle. Unlike TAQMAN® probes, Molecular Beacons, which form a stem-loop structure when free in solution, remain intact during the amplification reaction. Molecular Beacons fluoresce during hybridization when the fluorescent dye and the quencher are separated. For signal measurement to be effective, the fluor and quencher must rebind in every cycle. SCORPIONS® probes, which maintain a stem-loop configuration in the unhybridized state, has at its 3' end an additional sequence that is complementary to the extension product of the primer that is linked to the 5' end of a specific primer via a non-amplifiable monomer. After extension of the SCORPIONS® primer, the specific probe sequence is able to bind to its complement within the extended amplicon thus opening up the hairpin loop such that the fluor is no longer quenched and signal is seen. SYBR® Green probes binds double-stranded DNA and upon excitation emit light; thus as PCR product accumulates, fluorescence increases.

The term "singleplex" refers to a single assay that is not carried out simultaneously with any other assays. For example, within a multiwell plate, a singleplex assay refers to a single reaction that is performed within a single well of the multiwall plate. Singleplex assays include individual assays that are carried out sequentially.

The term "multiplex" refers to multiple assays that are carried out simultaneously. As used herein, a multiplex assay refers to the number of target sites that the assay aims to identify. For example, a multiplex assay that is designed to identify two sites is termed a dualplex assay. Within a multiwell plate, a multiplex assay performs multiple reactions within a single well of the multiwell plate.

As used herein, the term "oligonucleotide" refers to a molecule comprising two or more deoxyribonucleotides, ribonucleotides, and/or nucleotide analogs, the latter including nucleic acid analogs, such as isoguanosine, isocytosine, inosine, or deoxyinosine. The length of the oligonucleotide will vary depending on the function of the oligonucleotide. The oligonucleotide may be generated in any manner, including chemical synthesis, DNA replication, reverse transcription, PCR, or a combination thereof. As used herein, the term "oligonucleotide" is meant to encompass primers (both forward and reverse primers) and detection probes.

As used herein, the term "primer" refers to an oligonucleotide which, whether purified from a nucleic acid restriction digest or produced synthetically, is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase or the like, and at a suitable temperature and pH. The primer is preferably single stranded for maximum efficiency, but may alternatively be double stranded. If double stranded, the primer is first treated to separate its strands before being used to prepare extension products. The primer must be sufficiently long to prime the synthesis of extension products in the presence of the agents for polymerization. The exact lengths of the primers will depend on many factors, including temperature and the source of primer. For example, depending on the complexity of the target sequence, a primer typically contains 15 to 25 or more nucleotides, although it can contain fewer nucleotides. Short primer molecules generally require cooler temperatures to form sufficiently stable hybrid complexes with a template.

The term "forward primer" refers to a primer that forms an extension product by binding in the 5' to 3' direction to the 3' end of a strand of a denatured DNA analyte.

The term "reverse primer" refers to a primer that forms an extension product by binding in the 3' to 5' direction to the 5' end of a strand of a denatured DNA analyte.

The term "amplicon" refers to the amplification product of a nucleic acid extension assay, such as PCR.

As used herein, the term "probe" or "detection probe" refers to an oligonucleotide that forms a hybrid structure with a target sequence contained in a molecule (i.e., a "target molecule") in a sample undergoing analysis, due to complementarity of at least one sequence in the probe with the target sequence.

As used herein, the term "destabilizing oligonucleotide" is meant to refer to a primer that has a 5' segment that binds to a wild-type (WT) or mutant target sequence and a 3' segment that is genotype specific (i.e., specific to a particular WT or mutant SNP). The 5' segment of the destabilizing primer binds non-specifically to a WT or mutant sequence while the 3' segment binds to a specific WT or mutant SNP. The primer is destabilized by way of a polydeoxyinosine linker between the 5' segment and the 3' segment. When the 3' segment efficiently binds to a genotype specific segment, the 3' segment anchors the full length of the primer and allows for efficient extension of the target sequence. When the 3' segment does not bind efficiently to a genotype specific segment, the full length of the primer is destabilized thus causing either inefficient extension of the target sequence or no extension at all.

The term "pseudogene" refers to non-functional genes that closely resemble functional genes. Over the course of evolution, pseudogenes have lost their protein-coding ability or are otherwise no longer expressed in the cell. Due to their close physical resemblance to known functional genes, "pseudogene amplification" is sometimes observed in amplification assays.

As used herein, the term "melting temperature" (Tm) in relation to an oligonucleotide is defined as the temperature at which 50% of the DNA forms a stable double-helix and the other 50% has been separated into single stranded molecules. As known to those of skill in the art, PCR annealing temperature is typically a few degrees less than the Tm, the latter of which is calculated based on oligo and salt concentrations in the reaction.

The term "biological sample" as used herein is meant to include both human and animal species.

The term "gene" refers to a particular nucleic acid sequence within a DNA molecule that occupies a precise locus on a chromosome and is capable of self-replication by coding for a specific polypeptide chain. The term "genome" refers to a complete set of genes in the chromosomes of each cell of a specific organism.

The term "target" refers to a molecule, gene, or genome containing a nucleotide, nucleic acid sequence, or sequence segment that is intended to be characterized by way of detection, amplification, or quantification.

The term "single nucleotide polymorphism" or "SNP" refers to single point variations in genomic DNA or tumor-associated DNA. It is to be understood that within the context of the present invention, the terms "mutation" and "point mutation" are meant to include and/or refer to SNPs.

Single nucleotide polymorphisms (SNPs) in KRAS codons 12, 13, and 61 and PIK3CA codons 542, 545, and 1047 are difficult to distinguish using conventional oligonucleotides. The present invention overcomes this difficulty by providing non-conventional oligonucleotides, which may be used in kPCR genotyping assays to detect KRAS codon 12, 13, and 61 mutations (see, FIG. 2A-2C) and PIK3CA exon 9 and exon 20 mutations (see, FIG. 8) with high specificity.

The codon 12 KRAS mutations that may be genotyped using the non-conventional oligonucleotides of the present invention are selected from the group consisting of Gly12Asp (GGT>GAT), Gly12Ala (GGT>GCT), Gly12Val (GGT>GTT), Gly12Ser (GGT>AGT), Gly12Arg (GGT>CGT), and Gly12Cys (GGT>TGT). The codon 13 KRAS mutation that may be genotyped using the non-conventional oligonucleotides of the present invention is Gly13Asp(GGC>GAC) and the codon 61 KRAS mutation that may be genotyped using the non-conventional oligonucleotides of the present invention is Gln61Leu (CAA>CTA).

The codon 542 PIK3CA mutation that may be genotyped using the non-conventional oligonucleotides of the present invention is Glu542Lys (GAA>AAA); the codon 545 PIK3CA mutations that may be genotyped using the non-conventional oligonucleotides of the present invention are selected from Glu545Lys (GAG>AAG) and Glu545Asp (GAG>GAT); and the codon 1047 PIK3CA mutation that may be genotyped using the non-conventional oligonucleotides of the present invention is His1047Arg (CAT>CGT).

The non-conventional oligonucleotides of the present invention may be used as a forward primer, reverse primer, or detection probe. The non-conventional oligonucleotides of the present invention typically have a non-specific 5' segment of 15-35 bases in length that is complementary to a target sequence, a genotype specific 3' segment of 3-5 bases, and a polydeoxyinosine linker of 3-5 bases in length that separates the 5' segment from the 3' segment. While the 5' segment of the oligonucleotides of the present invention is preferably 20-25 bases in length, it is to be understood that the 5' segment may range from 15-35 bases in length.

In one embodiment of the invention, the oligonucleotide is used as a forward primer in kPCR assays to detect KRAS codon 12, 13, and 61 mutations and PIK3CA codon 542, 545, and 1047 mutations. In another embodiment of the invention, the oligonucleotide is used as a reverse primer or detection probe to avoid pseudogene amplification (see, Example 9).

In a further embodiments of the invention, the 5' segment of the oligonucleotides has a Tm in the range of 50-65° C.; the 3' segment has a Tm<10° C.; and the polydeoxyinosine linker of the oligonucleotides has a Tm<10° C. In some embodiments of the invention, it is to be understood that it may be preferable for the 5' segment of the oligonucleotide to have a Tm in the range of 50-60° C. or 50-55° C.

The 5' segment of the forward primer is designed with a high annealing temperature (i.e., >50° C.) to assure specific annealing of the primer to its matched target. The SNP-specific sequence is designed with a low annealing temperature at the 3' segment of the primer which is separated from the 5' segment by the polydeoxyinosine linkers, which form a destabilizing region in the forward primers adjacent to the 3' segment. Due to the destabilizing nature of the polydeoxyinosine linker, the Tm of the primer is lower than an equivalent primer without the polydeoxyinosine linker. A lower Tm allows the 5' segment of the polydeoxyinosine linked primers to hybridize to the target while the 3' segment remains highly specific for the SNP site due to the short unstable 3' segment. In use, the polydeoxyinosine linker and the 3' segment will flank over mismatches in the SNP sites prohibiting the elongation step of the PCR reaction. The oligonucleotide of the present invention does not have three distinct Tm priming regions as the 3' segment cannot be considered a viable priming portion of the oligonucleotide.

The present invention also provides methods of detecting KRAS mutations at codons 12, 13, and 61 and PIK3CA mutations at codons 542, 545, and 1047 comprising the steps of: extracting DNA from a biological sample; assaying the DNA via kPCR for the mutant DNA using the destabilizing oligonucleotide of the present invention as a forward primer against a background of wild-type DNA. In one embodiment of the invention, the KRAS and/or PIK3CA kPCR Genotyping Assays are conducted in singleplex format to detect one mutation. In another embodiment of the invention, the KRAS and/or PIK3CA kPCR Genotyping Assays are conducted in multiplex format to detect two or more mutations. Example 7 shows the use of the PIK3CA kPCR Genotyping Assay to detect codon 542 and 1047 PIK3CA mutations in a dualplex format.

Example 4 shows how the KRAS kPCR and Genotyping Assay of the present invention is able to achieve mutant selective detection of less than 1:100 (<1%) of KRAS codon 12 or 13 mutants in a background of KRAS wild-type codons 12 and 13 (Table 14). By contrast, the prior sequencing method and the commercially available THERASCREEN® KRAS Mutation Kit have a detection capability of approximately 15% and 1% KRAS codon 12 and 13 mutant sequences, respectively, in a background of wild-type DNA.

Example 5 shows a comparison of the KRAS kPCR Genotyping Assay of the present invention versus the prior sequencing method and THERASCREEN® KRAS Mutation Detection system as applied to fresh frozen clinical sample DNA extracts from patients with CRC. As shown in Tables 15-17, the KRAS kPCR Genotyping Assay of the present invention was capable of detecting mutants with higher sensitivity in smaller sample sizes (see, Table 17). As previously discussed, the high mutant selective ability of the forward primer is the result of the 3-5 consecutive destabilizing deoxyinosines acting as a structure to ensure the amplification of the mutant sequence with either low efficiency or no unspecific sequences, e.g., the wild-type sequences.

Figure 4:
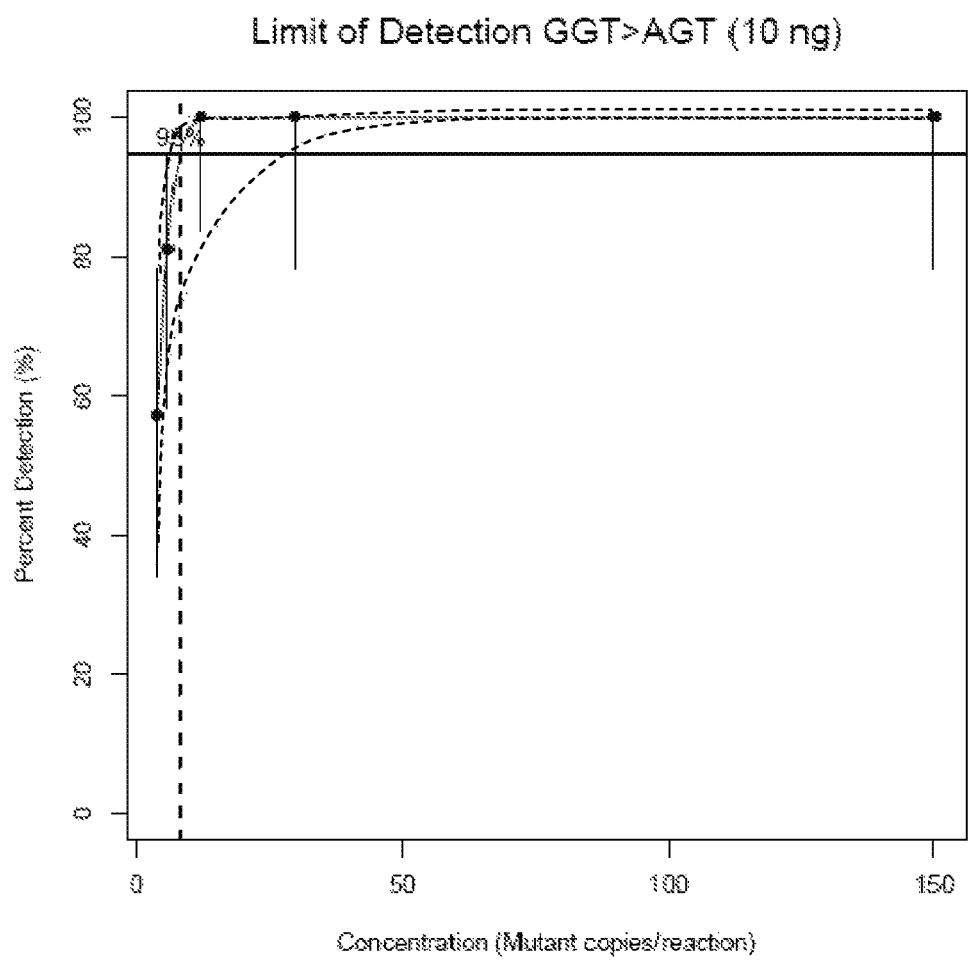
Figure 5:
Figure 6:
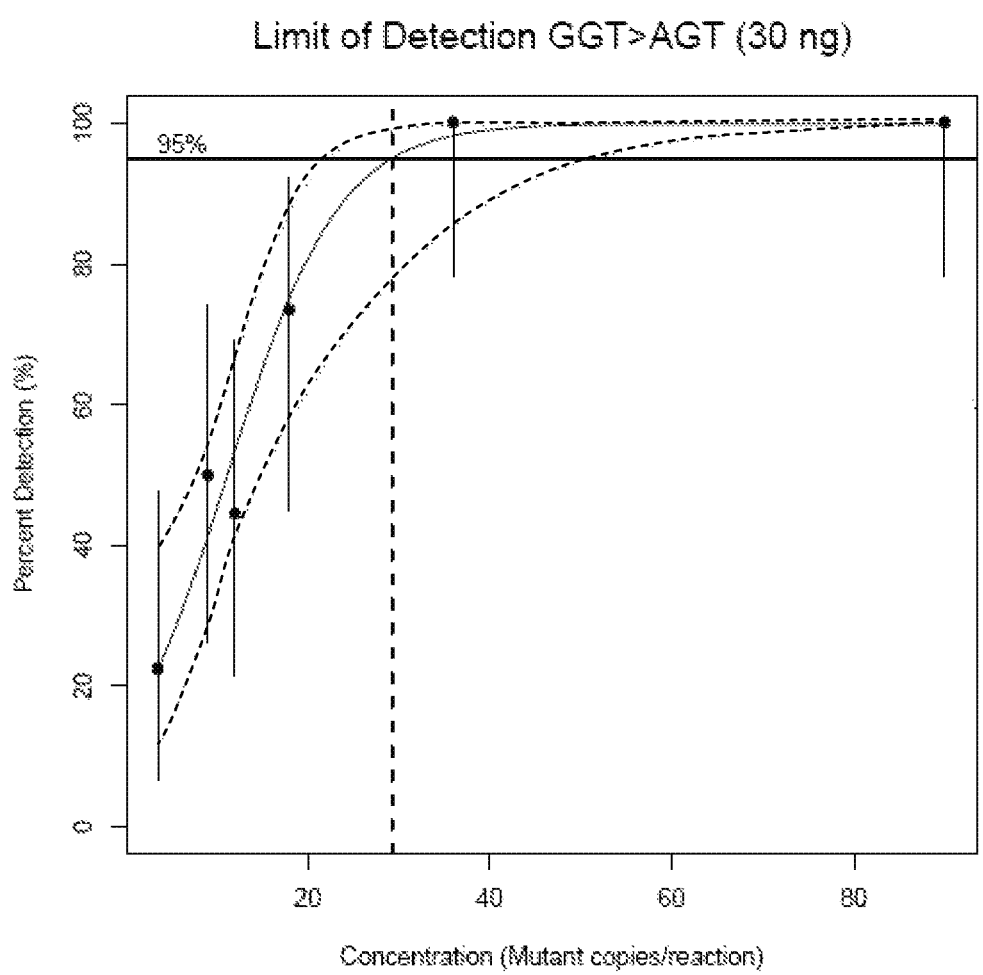

The sensitivity of the KRAS and PIK3CA kPCR Genotyping Assays of the present invention may be determined via a cycle threshold ("Ct") readout based on the specificity of a kPCR probe binding to the PCR product; the binding indicating successful extension from one of the forward primers designed to amplify the SNP sequence (see, Examples 3 and 4). The kPCR probe used in the Examples is a TAQMAN® probe; however, it is to be understood that the kPCR genotyping assays of the present invention may be used with any suitable kPCR probe. A Ct cutoff value is assigned for the difference between the Ct value generated for the amplification control (wild-type) and the presence of a positive Ct value generated for any of the matched mutant assays included in the test (see, FIGS. 3-6; Examples 3 and 4). The Ct readout system of the present invention has the advantage of being constant for each assay performed (see, Example 3, Table 8); accordingly, unlike the THERASCREEN® KRAS Mutation Detection system, the cutoff for each assay of the present invention is constant, rather than variable.

The destabilizing oligonucleotide of the present invention may also be used to preventing pseudogene amplification (see, Example 9). The method of present pseudogene amplification comprises the steps of: identifying at least one sequence of interest of a gene; identifying at least one homolog with less than 100% similarity to the at least one sequence of interest; identifying chromosome locations of the at least one sequence of interest and the at least one homolog, wherein the at least one sequence of interest and the at least one homolog are located on different chromosomes; identifying nucleotide sequence mismatch sites on the at least one sequence of interest and the at least one homolog; hybridizing the destabilizing oligonucleotide of the present invention to the nucleotide sequence mismatch sites on the at least one sequence of interest; amplifying the at least one sequence of interest, wherein amplicons resulting from the kPCR assay show no homolog amplification.

In one embodiment of the invention, the gene is PIK3CA on chromosome 3 and the at least one sequence of interest is located on exon 9 of the PIK3CA gene.

In another embodiment of the invention, the at least one sequence of interest is an exon 9 PIK3CA mutant gene selected from the group consisting of Glu542Lys (GAA>AAA), Glu545Lys (GAG>AAG) and Glu545Asp (GAG>GAT). In a further embodiment of the invention, the at least one homolog is a pseudogene located on chromosome 22, chromosome 16, or both (See, FIG. 9 and Example 9).

In yet another embodiment of the invention, the oligonucleotide is a reverse primer that hybridizes to a nucleotide sequence mismatch site on the at least one sequence of interest.

In still another embodiment of the invention, the oligonucleotide is a detection probe that hybridizes to the nucleotide sequence mismatch site on the at least one sequence of interest.

In further embodiments of the invention, the reverse primer has a nucleotide sequence as set forth in SEQ ID NO. 17 and the detection probe has a nucleotide sequence as set forth in SEQ ID NO. 18 (See, Example 6, Table 16).

The present invention finds utility in a variety of applications, including without limitation, as a diagnostic method in order to determine if a cancer patient will be responsive to anti-EGFR monoclonal antibody therapy. Because patients with KRAS codon 12, 13, or 61 mutations or PIK3CA codon 542, 545, and 1047 mutations have been found to be non-responsive to anti-EGFR monoclonal antibody therapy, the kPCR Genotyping Assays of the present invention may prevent patients from undergoing ineffective therapy for conditions, such as mCRC or other cancers. In addition to being a diagnostic tool for determining cancer patient responsiveness to anti-EGFR therapy, the present invention also has utility in diagnosing a human or animal that has not been diagnosed with cancer for KRAS and/or PIK3CA mutations.

The kPCR genotyping assays described herein have the ability to accurately genotype genomic DNA extracts for KRAS codon 12, 13, and 61 mutations or PIK3CA codon 542, 545, and 1047 mutations from a variety of biological sample types, such as formalin-fixed paraffin embedded (FFPE) tissue, fresh frozen tumor specific tissue, circulating tumor cells, circulating cell-associated DNA from plasma, and circulating non-cell associated DNA from plasma. As discussed above, the KRAS and PIK3CA kPCR Genotyping Assays described herein are designed to achieve a higher sensitivity and specificity than conventional sequencing assays and may be used to genotype samples that have <1% mutant genes in a background of wild-type DNA.

The kPCR genotyping assays of the present invention also have the capability to be used as a screening tool for healthy patients to determine if they have KRAS mutations that could predict that onset of cancer. Because such healthy individuals would not have a tumor to biopsy, tissue testing would not be possible; however, the kPCR genotyping assay of the present invention may be performed on the healthy individuals plasma DNA, including circulating cell-associated plasma DNA and circulating non-cell associated plasma DNA.

As will be appreciated by those of skill in the art, the KRAS and PIK3CA oligonucleotides and kPCR genotyping methods of the present invention have additional utility in commercial diagnostic kits.

In one embodiment of the invention, there is provided a kPCR kit for detecting KRAS mutations, comprising kPCR reagent mixes for detection of KRAS mutations at one or more of codons 12, 13, and 61, comprising the KRAS oligonucleotide of the present invention; Taq polymerase; and instructions for use. The reagent mixes in the KRAS kit may be prepared for singleplex or multiplex detection of the codon 12, 13, and 61 mutations. In a singleplex format, each reagent mix will include oligonucleotides specific to each of the codon 12, 13, and 61 KRAS mutations. By contrast, in a multiplex format, the reagent mixes may include oligonucleotides specific to two or more of the codon 12, 13, and 61 KRAS mutations.

In another embodiment of the invention, there is provided a kPCR kit for detecting PIK3CA mutations, comprising kPCR reagent mixes for detection of PIK3CA mutations at one or more of codons 542, 545, and 1047, comprising the PIK3CA oligonucleotide of the present invention; Taq polymerase; and instructions for use. The reagent mixes in the PIK3CA kit may be prepared for singleplex or multiplex detection of the codon 542, 545, and 1047 mutations. In a singleplex format, each reagent mix will include oligonucleotides specific to each of the codon 542, 545, and 1047 PIK3CA mutations. By contrast, in a multiplex format, the reagent mixes may include oligonucleotides specific to two or more of the codon 542, 545, and 1047 PIK3CA mutations.

In a further embodiment of the invention, there is provided A kPCR kit for detecting if a patient is responsive to anti-EGFR therapy, comprising kPCR reagent mixes for detection of KRAS mutations at one or more of codons 12, 13, and 61, comprising the KRAS oligonucleotide of the present invention; kPCR reagent mixes for detection of PIK3CA mutations at one or more of codons 542, 545, and 1047, comprising the PIK3CA oligonucleotide of the present invention; Taq polymerase; and instructions for use. The KRAS reagent mixes and the PIK3CA reagent mixes in the KRAS/PIK3CA kit may each be individually prepared for singleplex or multiplex detection of KRAS and PIK3CA mutations, respectively. In a singleplex format, the KRAS/PIK3CA kit would include individual KRAS reagent mixes comprising oligonucleotides specific to each of the codon 12, 13, and 61 KRAS mutations and individual PIK3CA reagent mixes comprising oligonucleotides specific to each of the codon 542, 545, and 1047 PIK3CA mutations. In a multiplex format, the individual KRAS reagent mixes may include oligonucleotides specific to two or more of the codon 12, 13, and 61 KRAS mutations and the individual PIK3CA reagent mixes may include oligonucleotides specific to two or more of the codon 542, 545, and 1047 PIK3CA mutations. It is to be understood that the KRAS/PIK3CA kit may include a combination of reagent mixes for singleplex and multiplex screening. For example, a KRAS/PIK3CA kit may include reagent mixes for singleplex screening of KRAS and multiplex screening of PIK3CA.

Lastly, it is also to be understood that the kits of the present invention need not include reagent mixes for all of the KRAS and PIK3CA mutations described herein, but may include reagent mixes for single mutations or multiple mutations in various combinations.

It is to be understood that while the invention has been described in conjunction with the embodiments set forth above, the foregoing description as well as the examples that follow are intended to illustrate and not limit the scope of the invention.

All patents and publications mentioned herein are incorporated by reference in their entireties.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

In the following examples, genomic DNA was extracted using the QIAamp DNA Mini Kit (Cat #51306) (Qiagen, Valencia, Calif., USA).

kPCR singleplex assays were developed to run on a 96-well plate in a VERSANT® Amplification Detection Thermocycler (Siemens Healthcare Diagnostics, Inc., Deerfield, Ill., USA) based on the STRATAGEN® Mx3000P/MX3005P Real-Time PCR System (Stratagene, La Jolla, Calif., USA). The kPCR assays were run with TAQMAN® probes (Roche Molecular Systems, Alameda, Calif., USA) and AMPLITAQ® GOLD Polymerase (Roche Molecular Systems, Alameda, Calif., USA). The dNTP mix required for the kPCR assays were obtained from Applied Biosystems, Foster City, Calif., USA). The following dyes used as labeled probes in the kPCR assays were all obtained from Biosearch Technologies, Inc., Novato, Calif., USA: CY5® Direct (Cyanine Dye); HEX (fluorescein Dye); and FAM (fluorescein Dye). ROX (Passive Reference Dye) was obtained from Stratagene, La Jolla, Calif., USA).

Melting temperature ("Tm") estimations were made using the Integrated DNA Technologies (Coralville, Iowa, USA) on-line Tm tool (OligoAnalyzer 3.1 at default settings).

All forward and reverse primer pairs were determined using the National Center for Biotechnology Information primer designing tool (Primer BLAST). The database selected for the "Primer Pair Specificity Checking Parameters" was "Genome (chromosomes from all organisms)."

Example 1

Location of KRAD kPCR Genotyping Assay Primers and Probes

NCBI Accession No. NT_009714.16/Hs12_9871 was used to extract the KRAS genomic sequences.

The sequence in FIG. 1 shows the fragment of the KRAS genomic DNA cloned into a pCR II vector and used for quantifying KRAS DNA in samples. The location and design of the primer and probe candidates in the codon 12 and 13 KRAS kPCR Genotyping Assay are indicated on the sequence of FIG. 1 as follows:

The gray shaded region of the sequence is KRAS exon 2.

The bold underlined region of the sequence (ggtggc) is the location of KRAS codons 12 and 13.

The bold non-italicized area of the sequence (including the underlined region of the sequence) shows the location of the forward primers, including all wild-type and genotype-specific primers.

The bold italicized area of the sequence shows the location of the probe.

The unbolded underlined area of the sequence shows the location of reverse primer.

FIG. 2A identifies the sequences and map location (Accession #NT_009714.16/Hs12_9871) for the KRAS codon 12 wild-type forward primer, the six KRAS codon 12 mutant forward primers, a single KRAS codon 13 mutant primer, the KRAS exon 2 probe, the KRAS exon 2 forward primer, and the KRAS reverse primer. As shown in FIG. 2A, the forward primer design for the KRAS codon 12 set include the following characteristics: the 5' end of the forward primer is the same nucleotide sequence for all of the KRAS mutations (i.e., SEQ ID NOs. 1-8 have a 5' segment of ATGACTGAATATAAACTTGTGGTAGT (SEQ ID NO: 39)) while the number of polydeoxyinosine nucleotides or target specific bases on the 3' end may differ.

FIG. 2B identifies the sequences and map location (Accession #NT_009714.16/Hs12_9871) for the KRAS codon 61 wild-type forward primer, a single KRAS codon 61 mutant primer, the KRAS codon 61 reverse primer, and the KRAS codon 61 probe. The point mutations (i.e., SNPs) in the KRAS forward primers in FIGS. 2A and 2B are indicated with bold underlining.

FIG. 2C identifies the location of the KRAS codon 61 primers and probes of the present invention. The portion of the sequence between map location 18140458-18140399 is identified as follows: the bold portion 4409 identifies the 5' non-specific binding segment of the KRAS codon 61 forward primer; the non-bold underlined portion identifies the location of the polydeoxyinosine linker; and the bold underlined portion of the sequence identifies the 3' SNP-specific end.

Table 1 lists several of the KRAS primers from FIG. 2A, the name of the corresponding forward primer, the amino acid shorthand for the mutation, and the mutant variant shorthand. The only forward primer with efficient extension on the KRAS codon 12 wild-type target is the WT forward primer. The KRAS primers and probes were obtained from Biosearch Technologies, Inc., Novato, Calif., USA.

TABLE 1

| Sequence Name | Forward Primer | Amino Acid Shorthand | Mutant Variants |
|---|---|---|---|
| KRAS12_WT_GGT | WT forward primer | | |
| KRAS12_Mut_AGT | G12S specific forward primer | Gly12Ser | GGT > AGT |
| KRAS12_Mut_CGT | G12R specific forward primer | Gly12Arg | GGT > CGT |
| KRAS12_Mut_TGT | G12C specific forward primer | Gly12Cys | GGT > TGT |
| KRAS12_Mut_GAT | G12D specific forward primer | Gly12Asp | GGT > GAT |
| KRAS12_Mut_GCT | G12A specific forward primer | Gly12Ala | GGT > GCT |
| KRAS12_Mut_GTT (1) | G12V specific forward primer1 | Gly12Val | GGT > GTT |
| KRAS12_Mut_GTT (2) | G12V specific forward primer2 | Gly12Val | GGT > GTT |
| KRAS13_Mut_GAC | G13D specific forward primer | Gly13Asp | GGT > GAC |

Example 2

KRAS (Codon 12 and 13) kPCR Genotyping Assay Set-Up

The singleplex assay was set up with eight individual kPCR reaction mixes that were each loaded in one of the 8 rows of a 96-well plate. The reaction mixes contained PCR buffer, magnesium chloride, deoxyribonucleotide triphosphates, reference dye-ROX, specific oligonucleotides, fluorescence labeled oligonucleotide probe, and nuclease-free water. The Taq DNA polymerase was added to each reaction mix at the time of the assay. The following assays were run: KRAS codon 12 and 13 wild-type assays, all six KRAS codon 12 mutation assays (Gly12Ser, Gly12Arg, Gly12Cys, Gly12Asp, Gly12Ala, Gly12Val) and one codon 13 mutation assay (Gly13Asp).

The controls for each run included a contamination control (negative control), 100% KRAS codon 12 and 13 wild-type control (4 ng/uL), and one well of each of the six KRAS codon 12 mutations and the one KRAS codon 13 mutations, each diluted 1:100 in a background of KRAS codon 12 and 13 wild-type (4 ng/uL). The controls were loaded into columns 1, 2, and 3, leaving the remaining 9 columns for unknown samples. The assay was designed so that 5 ul of each sample and control was added to each of the 8 wells in a column to be tested by all of the assays. The KRAS kPCR assay was run with the following conditions:

KRAS kPCR Master Mix Formulation:

Reaction Mix final vol. (µL): 20 µL

Sample vol. (µL): 5 µL

Total Rxn vol (µL): 25 µL

Filter Gain Settings:

| | |
|---|---|
| CY5 ® Direct (Cyanine Dye) | 1X |
| ROX (Passive Reference Dye) | 1X |
| HEX (fluorescein Dye) | 1X |
| FAM (fluorescein Dye) | 8X |

TABLE 2

Thermal profile for KRAS kPCR Genotyping Assay

| | Temp. | Time | Cycles | Data Collection |
|---|---|---|---|---|
| AMPLITAQ ® Activation | 95° C. | 10 min. | 1 | |
| kPCR Cycles | 94° C. | 30 sec. | | |
| | 66° C. | 45 sec. (end pt = 3) | 50 | ROX, FAM |
| | 72° C. | 30 sec. | | |

Tables 3 and 4 set forth the PreMaster Mix and the Forward Primer Reaction Mix that were used to run the kPCR assay described herein. As indicated above, the Reaction Mix final volume is 20 µL. Table 4 shows a final reaction volume of 19.75 µL; this volume is mixed with 0.25 µL of Taq polymerase for a total volume of 20 µL.

TABLE 3

Premaster Mix for all Reactions

| Reagent | Starting conc | Final conc | Vol/Rxn (µL) |
|---|---|---|---|
| TAQMAN ® buffer | 10X | 1X | 2.5 |
| MgCl$_2$ | 25 mM | 3.500 mM | 3.5 |
| dNTP mix | 10 mM | 0.300 mM | 0.75 |
| ROX Internal Standard 1 mM | 1 mM | 0.050 µM | 0.13 |
| KRAS FAM-labeled probe* | 10 µM | 0.200 µM | 0.50 |
| KRAS reverse primer* | 10 µM | 0.100 µM | 0.25 |
| Water | | | 15.38 |
| Reaction Mix vol (µL) | | | 19.50 |

*Biosearch Technologies, Inc., Novato, CA, USA

TABLE 4

Reaction Mix for Forward Primers

| Reaction Mix ID | Reagent | Start Conc | Final Conc | Vol/Rxn (µL) |
|---|---|---|---|---|
| | PreMaster Mix | | | 19.50 |
| WT (GTT) | KRAS12_WT* | 10 µM | 0.100 µM | 0.25 |
| Mut (AGT) | K12Mut_AGT* | | | |
| Mut (CGT) | K12Mut_CGT* | | | |
| Mut (TGT) | K12Mut_TGT* | | | |
| Mut (GAT) | KRAS12MutPf2b* | | | |
| Mut (GCT) | KRAS12MutPf5b* | | | |
| Mut (GTT) | K12Mut_GTT* | | | |
| MutK13 (GAC) | KRAS13MutPf2a* | | | |
| | Rxn Mix vol (µL) | | | 19.75 |

*Biosearch Technologies, Inc., Novato, CA, USA

Table 5 shows the recommended plate layout for the KRAS kPCR Genotyping Assay (S.#=Sample).

TABLE 5

Recommended Plate Layout for KRAS kPCR Genotyping Assay

| Assay Rx Mix | | 1 | 2 | 3 | 4 | 5 | 6 | 7 | 8 | 9 | 10 | 11 | 12 |
|---|---|---|---|---|---|---|---|---|---|---|---|---|---|
| WT-Gly (GGT) | A | 100% WT | NTC | 100% WT | S.1 | S.2 | S.3 | S.4 | S.5 | S.6 | S.7 | S.8 | S.9 |
| 12SER (AGT) | B | K12mut 1:100 ATG | NTC | 100% WT | S.1 | S.2 | S.3 | S.4 | S.5 | S.6 | S.7 | S.8 | S.9 |
| 12ASP (GAT) | C | K12mut 1:100 GAT | NTC | 100% WT | S.1 | S.2 | S.3 | S.4 | S.5 | S.6 | S.7 | S.8 | S.9 |
| 12CYS (TGT) | D | K12mut 1:100 TGT | NTC | 100% WT | S.1 | S.2 | S.3 | S.4 | S.5 | S.6 | S.7 | S.8 | S.9 |
| 12VAL (GTT) | E | K12mut 1:100 GTT | NTC | 100% WT | S.1 | S.2 | S.3 | S.4 | S.5 | S.6 | S.7 | S.8 | S.9 |
| 12 ALA (GCT) | F | K12mut 1:100 GCT | NTC | 100% WT | S.1 | S.2 | S.3 | S.4 | S.5 | S.6 | S.7 | S.8 | S.9 |
| 12ARG (CGT) | G | K12mut 1:100 CGT | NTC | 100% WT | S.1 | S.2 | S.3 | S.4 | S.5 | S.6 | S.7 | S.8 | S.9 |
| 13ASP (GAC) | H | K13mut 1:100 GAC | NTC | 100% WT | S.1 | S.2 | S.3 | S.4 | S.5 | S.6 | S.7 | S.8 | S.9 |

Example 3

Sensitivity of the KRAS kPCR Genotyping Assay

The experiment described herein was conducted to establish assay sensitivity and specificity confidence. The experiment included optimizing the KRAS kPCR Genotyping Assay wild-type/mutant signal threshold and evaluating the assay sensitivity and specificity confidence using the optimized kPCR wild-type/mutant signal threshold.

The following two representative KRAS codon 12 mutants were examined: Gly12Val (GGT>GTT) and Gly12Ser (GGT>AGT). 5 µL of each sample was loaded in 8 wells and tested by 8 target specific master mixes.

Genomic DNA was extracted from cell cultures carrying sequences of wild-type (Gly12) and Gly12Val and Gly12Ser mutants. Genomic extracts were initially quantified by absorbance spectrophotometry then diluted to 20 ng/µL. The dilution accuracy of each extract was verified by a second optical density photospectrometry quantitation. KRAS copy number for each cell line was calculated by quantitating 100 ng of genomic extracts against the plasmid containing the KRAS-specific fragment. Using a previously acquired conversion number of 330 KRAS copies per ng, each cell extract was normalized to 660 copies/µL (2 ng/µL or 10 ng/reaction) and 1980 copies/µL (6 ng/µL or 30 ng/reaction). Two levels of total genomic DNA input were chosen to mimic low and high circulating genomic DNA in plasma from patients: (i) 2 ng total genomic DNA per µL (equivalent to 175 ng of circulating DNA in 1 mL of plasma with 80% sample preparation recovery) and (ii) 6 ng genomic DNA per µL (equivalent to 525 ng/mL). Test panels were diluted based on mutant template prevalence. Panel member mutant prevalence levels were chosen to determine assay sensitivity at 95% mutant detection rate. Panel information for the KRAS mutants is set forth in Table 7.

TABLE 7

Panel Member Information

| Total Genomic DNA Input per Reaction | Panel Members | Panel Member Description (Mutant Prevalence) | Mutant Copies | Replicates |
|---|---|---|---|---|
| 10 ng | 1 | 1:20 GGT > AGT (5%) | 150 | 15 |
| | 2 | 1:100 GGT > AGT (1%)v | 30 | 15 |
| | 3 | 1:250 GGT > AGT (0.4%) | 12 | 21 |
| | 4 | 1:500 GGT > AGT (0.2%) | 6 | 21 |
| | 5 | 1:750 GGT > AGT (0.13%) | 4 | 21 |
| | 6 | 1:20 GGT > GTT (5%) | 150 | 15 |
| | 7 | 1:100 GGT > GTT (1%) | 30 | 15 |
| | 8 | 1:250 GGT > GTT (0.4%) | 12 | 21 |
| | 9 | 1:500 GGT > GTT (0.2%) | 6 | 21 |
| | 10 | 1:750 GGT > GTT (0.13%) | 4 | 21 |
| | 11 | Control Wild-type (GGT) (0%) | 0 | 30 |
| 30 ng | 12 | 1:100 GGT > AGT (1%) | 90 | 15 |
| | 13 | 1:250 GGT > AGT (0.4%) | 36 | 15 |
| | 14 | 1:500 GGT > AGT (0.2%) | 18 | 15 |
| | 15 | 1:750 GGT > AGT (0.13%) | 12 | 18 |
| | 16 | 1:1000 GGT > AGT (0.1%) | 9 | 18 |
| | 17 | 1:2000 GGT > AGT (0.04%) | 3.6 | 18 |
| | 18 | 1:100 GGT > GTT (1%) | 90 | 15 |
| | 19 | 1:250 GGT > GTT (0.4%) | 36 | 15 |
| | 20 | 1:500 GGT > GTT (0.2%) | 18 | 15 |
| | 21 | 1:750 GGT > GTT (0.13%) | 12 | 18 |
| | 22 | 1:1000 GGT > GTT (0.1%) | 9 | 18 |
| | 23 | 1:2000 GGT > GTT (0.04%) | 3.6 | 18 |
| | 24 | Control Wild-type (GGT) (0%) | 0 | 18 |

*Total of 36 kPCR 96 well plates required.

Table 8 shows the Limits of Detection (LoD) and the 95% Confidence Intervals for the KRAS mutant variants of Table 7. The 95% Confidence Intervals, which were used to determine the Ct cutoff value for the mutant variants, include the Lower Critical Limit (LCL) and the Upper Critical Limit (UCL).

TABLE 8

LoD Based on Mutant Variant and Cutoff

| Mutant Variant | Ct Cutoff Value | Genomic Extract Concentration | LoD (Mutant copies/ reaction) | 95% LCL of LoD (Mutant copies/ reaction) | 95% UCL of LoD (Mutant copies/ reaction) |
|---|---|---|---|---|---|
| GGT > AGT | 7.8 | 10 ng | 7.86 | 5.75 | 9.97 |
| GGT > AGT | 7.8 | 30 ng | 34.71 | 24.15 | 45.27 |
| GGT > GTT | 7.8 | 10 ng | 9.09 | 5.19 | 12.98 |
| GGT > GTT | 7.8 | 30 ng | 36.21 | 19.83 | 52.5 |
| GGT > AGT | 8.4 | 10 ng | 8.11 | 5.10 | 11.12 |
| GGT > AGT | 8.4 | 30 ng | 29.27 | 18.83 | 39.71 |
| GGT > GTT | 8.4 | 10 ng | 8.66 | 4.48 | 12.84 |
| GGT > GTT | 8.4 | 30 ng | 34.27 | 15.28 | 53.27 |
| GGT > AGT | 8.7 | 10 ng | 8.26 | 4.99 | 11.54 |
| GGT > AGT | 8.7 | 30 ng | 23.35 | 15.01 | 31.69 |
| GGT > GTT | 8.7 | 10 ng | 7.91 | 3.90 | 11.92 |
| GGT > GTT | 8.7 | 30 ng | 33.8 | 11.67 | 55.93 |
| GGT > AGT | 9.4 | 10 ng | 7.76 | 4.39 | 11.13 |
| GGT > AGT | 9.4 | 30 ng | 16.69 | 9.14 | 24.24 |
| GGT > GTT | 9.4 | 10 ng | 7.81 | 2.91 | 12.70 |
| GGT > GTT | 9.4 | 30 ng | 25.61 | 9.99 | 41.23 |

FIGS. 3-6 graphically illustrate the estimated LoD (mutant copies per reaction) and associated 95% Confidence Intervals for the mutant variants set forth in Table 8 at the 8.4 cutoff value. Table 9 sets forth the specificity of the KRAS kPCR Genotyping Assay for wild-type panel members 11 and 24 from Table 7.

TABLE 9

Specificity of the KRAS kPCR Genotyping Assay on WT Samples

| Panel Members | Number of Replicates | Number of Mutants Not Detected | % Specificity | 95% CI* |
|---|---|---|---|---|
| 11 | 30 | 30 | 100.0% | 90.5% |
| 24 | 18 | 17 | 94.4% | 76.2% |

*One-side confidence limit for % specificity.

FIGS. 3-6 and Table 9 show that at a Ct cutoff value of 8.4 yields >94.4% specificity and sensitivity between 1:500 (0.2%) to 1:250 (0.4%) mutant to wild-type ratio at total genomic input of 10 and 30 ng/reaction. The sample panels of FIGS. 3-6 show that the mutant to wild-type ratio determines the sensitivity of the assay, rather than the total genomic material per reaction.

Example 4

KRAS kPCR Genotyping Assay Analytical Methods

Data Analysis and Acceptance Criteria

Mutant detection determination was based on the kPCR Ct signal difference between the wild-type detection and each of the six codon 12 and one codon 13 mutant signals. Mutant signals were ranked from lowest to highest Ct value with a low Ct value indicating a large quantity of kPCR products. The lowest mutant signal was then compared to a Ct Cutoff Value, which is the maximum Ct difference between the wild-type signal and the mutant candidate signal considered valid. Only the lowest mutant signal that also satisfied the Ct Cutoff Value criterion was matched with the corresponding mutant specific kPCR treatment and genotyped. A data analysis flow chart is provided in Table 10. Table 11 shows the KRAS kPCR Genotyping Assay Plate Acceptance Criteria, Table 12 shows Ct values for the KRAS kPCR Genotyping Assay controls and two representative samples, Table 13 shows Ct Cutoff Values of the assay, and Table 14 provides a summary of the assay run.

TABLE 10

KRAS kPCR Genotyping Assay Analysis Schematic Diagram

| kPCR Signal | Possible Results | | | |
|---|---|---|---|---|
| Amplifiable DNA Signal | Yes | Yes | No | No |
| Detectable Mutant Signal | No | Yes | Yes | No |
| | ? ? Mutant Signal Filter ? | | ? ? | ? ? |
| | ? | ? | ? | ? |
| Genotyping Results | Wild-type | Mutant | | No Template |

TABLE 11

KRAS kPCR Genotyping Assay Plate Acceptance Criteria

| Well Column | Description | Plate Result | Reported Result | Notes |
|---|---|---|---|---|
| 1 | 10 ng 1:100 Mutant:WT Low Positive Detection Control | All wells detecting Ct values <40 | Valid Plate | The 1% mutant to wild-type template ratio was selected as a low positive control, and was expected to be detected approximately 100% of the time based on preliminary sensitivity experiments. Actual analytical sensitivity of the assay was determined to be between 0.25%-0.35% (95% LoD value) ÷ [330 × (Total Genomic Input)]. Must be positive for a valid plate. |

TABLE 11-continued

KRAS kPCR Genotyping Assay Plate Acceptance Criteria

| Column | Well Description | Plate Result | Reported Result | Notes |
|---|---|---|---|---|
| 2 | Contamination Control | All wells indicating "No Ct" | Valid Plate | Nuclease free water was used as negative control material. Must be negative for a valid plate. |
| 3 | 10 ng 100% WT Control | Strong Ct value at Well A3* | Valid Plate | Wild-type controls must be positive for a valid plate. |
| 4-9 | Sample of Interest | | Any of the 7 codon 12 and 13 mutations "Genotype," "Wild-type," or "No Template" | A mutant genotype result is valid only if a Ct value is reported in Row A and the lowest Ct value from Row B-H is within the Row A Ct value. It is likely that all patient derived genomic extracts will contain at least 50% wild-type template. A reported Ct must be within the differential Ct threshold for a valid test result. |

*The position of well A3 is indicated in Table 2.

TABLE 12

KRAS kPCR Genotyping Assay Analysis - Ct Values from Example Run File with Assay Controls and Two Representative Samples

| Sample | K12/13 WT GGTGGC | K12 Mutants | | | | | | | K13 Mutant |
|---|---|---|---|---|---|---|---|---|---|
| | | AGTGGC | GATGGC | TGTGGC | GTTGGC | GCTGGC | CGTGGC | GGTGAC | |
| 20 ng 1:100 Mutant:WT Control | 29.23* | 34.96* | 38.51* | 36.13* | 34.54* | 37.43* | 33.43* | 34.1* | |
| Contam. Control | No Ct+ | No Ct+ | No Ct+ | No Ct+ | No Ct+ | No Ct+ | No Ct+ | No Ct+ | |
| 20 ng 100% WT Control | 29.54++ | 43.04 | No Ct | No Ct | 40.31++ | No Ct | No Ct | No Ct | |
| Clinical sample 1 | 26.41† | 37.13† | No Ct | 45.47 | 38.4 | No Ct | No Ct | 38.21 | |
| Clinical sample 2 | 25.36‡ | 39.12 | 43.8 | 44.76 | 36.26 | 27.49‡ | 45.95 | 37.57 | |

TABLE 13 kPCR Genotyping Assay Analysis - Ct Cutoff Values

| Sample | Amplifiable DNA Signal | Ct Cutoff 8.4 K12 Signal | Ct Cutoff 7 K13 Signal | Ct Cutoff Genotyping |
|---|---|---|---|---|
| 20 ng 1:100 Mutant:WT Control | | | | N/A |
| Contamination Control | No Ct+ | No Ct | No Ct | No template |
| 20 ng 100% Wild-type Control | 29.54++ | No Ct | No Ct | Wild-type |
| Clinical sample 1 | 26.41† | No Ct | No Ct | Wild-type |
| Clinical sample 2 | 25.36‡ | 27.49‡ | No Ct | GCTGGC |

TABLE 14

Summary of Data Analysis Results

| Symbol | Well Description | Plate Result | Reported Result | Pass/Fail, Genotype |
|---|---|---|---|---|
| * | 20 ng 1:100 Mutant:WT Control | All wells detecting Ct values <40 | N/A | Pass |
| + | Contamination Control | All wells indicating "No Ct" | No Template | Pass |
| ++ | 20 ng 100% Wild-type Control | Strong Ct value at Well A3 | Wild-type | Pass |
| † | Clinical sample 1 | | Any of the 7 codon 12 and 13 mutant genotypes, "Wild-type," or "No Template" | Pass, Wild-type |

TABLE 14-continued

Summary of Data Analysis Results

| Symbol | Well Description | Plate Result | Reported Result | Pass/Fail, Genotype |
|---|---|---|---|---|
| ‡ | Clinical sample 2 | | Any of the 7 codon 12 and 13 mutant genotypes, "Wild-type," or "No Template" | Pass, GCTGGC |

Example 5

Comparison of KRAS kPCR Genotyping Assay Method Versus Sequencing and THERASCREEN® KRAS Mutation Kit Fourteen (14) previously characterized CRC fresh frozen clinical sample DNA extracts were tested for analytical accuracy with the KRAS kPCR Genotyping Assay described herein versus the THERASCREEN® KRAS Mutation Kit and standard sequencing (Table 15). Both assays detected mutations in 11/14 clinical tissue samples at an adjusted 20 ng/reaction input level. The KRAS kPCR Genotyping Assay detected mutations in 13/14 of these samples at a higher input level (100 ng/reaction); the remaining sample was determined to be wild-type by both assays as well as by standard sequencing (see, Table 15, clinical sample 14). The higher input level was not recommended for the THERASCREEN® KRAS Mutation Kit, presumably due to specificity limitations. With respect to the detected mutations from Table 15, clinical sample 8 resulted in a different mutation using the THERASCREEN® assay and KRAS kPCR genotyping assay of the present invention, the latter of which detected the same mutation, i.e., GGTGAC, in both 20 ng and 100 ng samples. The detection at the higher 100 ng concentration confirmed that the mutation detected at the lower concentration with the KRAS kPCR Genotyping Assay was accurate.

In addition to the 14 clinical samples, the kPCR genotyping assay of the present invention was also tested on the following duplicate panels: six (6) codon 12 mutant:wild-type panels and one (1) codon 13 mutant:wild-type panel (Table 16). The codon 12 and 13 duplicate panels were each spiked with known concentrations of wild-type and mutant DNA at 1:100 (1%) and 1:250 (0.4%). For direct comparison, each panel member was adjusted to 20 ng/reaction (4 ng/μL), which is the maximum recommended concentration for the THERASCREEN® KRAS Mutation Kit. As show in Table 17, the KRAS kPCR Genotyping Assay of the present invention detected mutations in 100% and 92.8% of the 1% and 0.4% diluted mutant panel members (see, Table 16), respectively, compared with 35.7% and 14.3% for the 1% and 0.4% diluted mutant panel members using the THERASCREEN® KRAS Mutation Kit.

TABLE 15

Results for Codon 12 & 13 Mutant:Wild-type on CRC Tumor Tissue DNA

| Sample ID (Clinical Samples) | TheraScreen® KRAS Mutation Kit 20 ng/rxn sample input Genotype | KRAS kPCR Genotyping Assay 20 ng/rxn sample input Genotype | KRAS kPCR Genotyping Assay 100 ng/rxn sample input Genotype | KRAS Standard Sequencing 100 ng/rxn sample input Genotype |
|---|---|---|---|---|
| Clinical 1 | GATGGC | GATGGC | GATGGC | GATGGC |
| Clinical 2 | GCTGGC | GCTGGC | GCTGGC | GCTGGC |
| Clinical 3 | GATGGC | GATGGC | GATGGC | GATGGC |
| Clinical 4 | TGTGGC | TGTGGC | TGTGGC | TGTGGC |
| Clinical 5 | No Mutant | No Mutant | GTTGGC | No Mutant |
| Clinical 6 | No Mutant | No Mutant | GTTGGC | GTTGGC |
| Clinical 7 | GCTGGC | GCTGGC | GCTGGC | GCTGGC |
| Clinical 8 | TGTGGC | GGTGAC | GGTGAC | No Mutant |
| Clinical 9 | GTTGGC | GTTGGC | GTTGGC | No Mutant |
| Clinical 10 | GGTGAC | GGTGAC | GGTGAC | GGTGAC |
| Clinical 11 | GTTGGC | GTTGGC | GTTGGC | No Mutant |
| Clinical 12 | GTTGGC | GTTGGC | GTTGGC | GTTGGC |
| Clinical 13 | GATGGC | GATGGC | GATGGC | GATGGC |
| Clinical 14 | No Mutant | No Mutant | No Mutant | No Mutant |

TABLE 16

Results for Codon 12 and 13 Mutant:Wild-type Dilution Panels

| Sample ID (for 6 codon 12 duplicates & 1 codon 13 duplicate) | TheraScreen® KRAS Mutation Kit Cell Line Panel Diluted 1:100 (1%) Genotype | KRAS kPCR Genotyping Assay Cell Line Panel Diluted 1:100 (1%) Genotype | TheraScreen® KRAS Mutation Kit Cell Line Panel Diluted 1:250 (0.4%) Genotype | KRAS kPCR Genotyping Assay Cell Line Panel Diluted 1:250 (0.4%) Genotype |
|---|---|---|---|---|
| Gly12Cys | No Mutant | TGTGGC | No Mutant | TGTGGC |
| GGT > TGT | No Mutant | TGTGGC | No Mutant | TGTGGC |
| Gly12Arg | CGTGGC | CGTGGC | CGTGGC | CGTGGC |
| GGT > CGT | CGTGGC | CGTGGC | No Mutant | CGTGGC |
| Gly12Ala | No Mutant | GCTGGC | No Mutant | GTTGGC |
| GGT > GCT | No Mutant | GCTGGC | No Mutant | GCTGGC |
| Gly12Ser | No Mutant | AGTGGC | No Mutant | AGTGGC |
| GGT > AGT | AGTGGC | AGTGGC | No Mutant | AGTGGC |
| Gly12Asp | No Mutant | GATGGC | No Mutant | GATGGC |
| GGT > GAT | No Mutant | GATGGC | No Mutant | GATGGC |
| Gly12Val | GTTGGC | GTTGGC | No Mutant | GTTGGC |

TABLE 16-continued

Results for Codon 12 and 13 Mutant:Wild-type Dilution Panels

| Sample ID (for 6 codon 12 duplicates & 1 codon 13 duplicate) | TheraScreen ® KRAS Mutation Kit Cell Line Panel Diluted 1:100 (1%) Genotype | KRAS kPCR Genotyping Assay Genotype | TheraScreen ® KRAS Mutation Kit Cell Line Panel Diluted 1:250 (0.4%) Genotype | KRAS kPCR Genotyping Assay Genotype |
|---|---|---|---|---|
| GGT > GTT | GTTGGC | GTTGGC | GTTGGC | GTTGGC |
| Gly13Asp | No Mutant | GGTGAC | No Mutant | No Mutant |
| GGC > GAC | No Mutant | GGTGAC | No Mutant | GGTGAC |

TABLE 17

Genotyping Results Summary for Dilution Panel and CRC Clinical Sample Extracts

| | TheraScreen ® KRAS Mutation Kit | KRAS kPCR Genotyping Assay |
|---|---|---|
| Mutant detected in clinical samples | 11/14 (20 ng/rxn) | 11/14 (20 ng/rxn) 13/14 (100 ng/rxn) |
| Mutant detected in dilution panel (1:100) | 5/14 (35.7%) | 14/14 (100%) |
| Mutant detected in dilution panel (1:250) | 2/14 (14.3%) | 13/14 (92.8%) |
| Mutant genotype mismatch (1:100) | 0/5 (0%) | 0/14 (0%) |
| Mutant genotype mismatch (1:250) | 0/2 (0%) | 1/13 (8%)* |

*mismatch detected for one duplicate sample of Gly12Ala (GGT > GCT) at 0.4% dilution Example 6

Location of PIK3CA kPCR Genotyping Assay Primers and Probes

NCBI Reference Sequence: NC_000003.11 was used to extract PIK3CA genomic sequences.

FIG. 7 shows the PIK3CA (Chromosome 3) oligonucleotide map with the following sequence characteristics:

Capital letters indicate exon regions.

Gray shaded bold italicized letters indicate nucleic acid of interest in the wild-type sequence.

Gray shaded non-italicized bold letters indicate the mismatch/insertion sites of chromosome 22.

Single-lined underlined sections of the sequence identify forward primer regions.

Double-lined underlined sections of the sequence identify probes.

Triple-lined underlined sections of the sequence identify reverse primer regions.

FIG. 8 identifies PIK3CA oligonucleotides from exon 9 and 20. Both exon 9 and 20 share exon specific fluorescent probe and reverse primers. Nucleic acids of interest in the wild-type and mutant sequences are identified with bold underlining and mismatch/insertion sites of chromosome 22 (see Example 9) are identified with gray shading (Exon 9 Reverse Primer 2 & Exon 9 Probe E).

Example 7

PIK3CA kPCR Genotyping Assay Set-Up

Pancreatic cancer cell line Hs766t (ATCC No. HTB-134) was used in the PIK3CA kPCR Genotyping Assay as a wild-type control because it harbors wild-type sequences in all three PIK3CA mutated codons: 542, 545, and 1047. Hs766t was also used for diluting mutants in mutant prevalence panels. The PIK3CA kPCR assay was run with the following conditions:

PIK3CA kPCR Master Mix formulation:

Reaction Mix final vol. (µL): 20 µL

Sample vol. (µL): 5 µL

Total Rxn vol (µL): 25 µL

Filter Gain Settings:

| CY5 ® Direct (Cyanine Dye) | 8X |
| ROX (Passive Reference Dye) | 1X |
| HEX (fluorescein Dye) | 4X |
| FAM (fluorescein Dye) | 8X |

TABLE 18

Thermal profile for PIK3CA kPCR Genotyping Assay

| | Temp. | Time | Cycles | Data Collection |
|---|---|---|---|---|
| AMPLITAQ ® Activation | 95° C. | 10 min. | 1 | |
| kPCR Cycles | 94° C. | 30 sec. | | |
| | 60° C. | 45 sec. (end pt = 2) | 50 | ROX, FAM |
| | 72° C. | 30 sec. | | |

Table 19 shows the recommended plate layout for the PIK3CA kPCR Genotyping Assay. In the table below, S.# refers to the sample number with each sample to be tested in four wells. The PIK3CA kPCR Genotyping Assay described herein consisted of four kPCR master mixes each occupying one well as follows (see Example 8, Table 20 for an explanation of the nucleotide substitution and amino acid change nomenclature for the exon 9 and 20 mutants):

I. Wild-type Exon 9 and Exon 20 Dualplex;

II. Exon 9 (G1624A:E542K) and Exon 20 (A3140G: H1047R) Dualplex;

III. Exon 9 (G1633A:E545K) Singleplex; and

IV. Exon 9 (G1635T:E545D) Singleplex.

TABLE 19

Recommended Plate Layout for PIK3CA kPCR Genotyping Assay

| Assay | | 1 | 2 | 3 | 4 | 5 | 6 | 7 | 8 | 9 | 10 | 11 | 12 |
|---|---|---|---|---|---|---|---|---|---|---|---|---|---|
| I   | A | S.1  | S.2  | S.3  | S.4  | S.5  | S.6  | S.7  | S.8  | S.9  | S.10 | S.11 | S.12 |
| II  | B | S.1  | S.2  | S.3  | S.4  | S.5  | S.6  | S.7  | S.8  | S.9  | S.10 | S.11 | S.12 |
| III | C | S.1  | S.2  | S.3  | S.4  | S.5  | S.6  | S.7  | S.8  | S.9  | S.10 | S.11 | S.12 |
| IV  | D | S.1  | S.2  | S.3  | S.4  | S.5  | S.6  | S.7  | S.8  | S.9  | S.10 | S.11 | S.12 |
| I   | E | S.13 | S.14 | S.15 | S.16 | S.17 | S.18 | S.19 | S.20 | S.21 | S.22 | S.23 | S.24 |
| II  | F | S.13 | S.14 | S.15 | S.16 | S.17 | S.18 | S.19 | S.20 | S.21 | S.22 | S.23 | S.24 |
| III | G | S.13 | S.14 | S.15 | S.16 | S.17 | S.18 | S.19 | S.20 | S.21 | S.22 | S.23 | S.24 |
| IV  | H | S.13 | S.14 | S.15 | S.16 | S.17 | S.18 | S.19 | S.20 | S.21 | S.22 | S.23 | S.24 |

The kPCR reaction volume was 250 µL per well, 20 µL master mix and 50 µL sample. Both exon 9 and 20 share exon specific fluorescent probe and reverse primers. Exon 9 and exon 20 fluorescent probes were FAM and HEX fluorophore-tagged, respectively, to differentiate kPCR signals.

Extraction and internal controls were incorporated into the assay to monitor extraction quality and kPCR performance. The extraction/internal control for the KRAS and PIK3CA kPCR assays described herein consisted of a short DNA fragment (MET-IC). The fluorophore of the MET-IC assay is CY5 so the HEX detection channel was not co-occupied by the exon 20 assay and the MET-IC assay. Because the design nature of the mutant selective primers, a strong MET-IC assay could out-compete the mutant detection assay signals; therefore, the MET-IC assay was limited so that either a MET-IC signal or any other true kPCR signal would validate the reaction. The current MET-IC assay condition was demonstrated to achieve 1:1000 mutant targets in a wild-type background.

Example 8

Sensitivity of the PIK3CA kPCR Genotyping Assay

The PIK3CA kPCR Genotyping Assay was developed to detect and assign a genotype when the mutant is present in approximately 0.4% (1:250) in a background of wild-type genomic DNA. Primers were designed to produce PCR products <160 bp to increase assay sensitivity on fragmented samples. Like the sensitive mutant forward primers in the KRAS kPCR Genotyping Assay, the mutant forward primers of the PIK3CA kPCR Genotyping Assay consist of a 5' fragment and a 3' fragment separated by a series of 3-5 destabilizing deoxyinosine bases acting as a polylinker.

Results of Primer BLAST showed that NCBI Reference Sequence: NC_000003.11 was the most likely amplified target across all assays. Table 20 shows the results (amplicon size) of a PIK3CA kPCR Genotyping Assay for Exon 9 (G1624A:E542K), Exon 9 (G1633A:E545K), Exon 9 (G1635T:E545D), and Exon 20 (A3140G, H1047R).

TABLE 20 kPCR Assay

| Exon | Nucleotide Substitution* | Amino Acid Change | Amplicon Size |
|---|---|---|---|
| Exon 9  |         | Wild-type assay | 127 bp |
| Exon 9  | G1624A  | E542K           | 150 bp |
| Exon 9  | G1633A  | E545K           | 139 bp |
| Exon 9  | G1635T  | E545D           | 139 bp |
| Exon 20 | A3140G  | H1047R          | 141 bp |

*Nucleotide change within the coding sequence.

Example 9

Pseudogene Challenge

One challenge of the exon 9 assay design is the existence of two pseudogenes on chromosome 16 and chromosome 22q11.2 (Cat Eye Syndrome region). Literature indicates that a homolog of 97% similarity exists in exons 9, 11-13, and partial exon 10 of the PIK3CA gene. During the design of the exon 9 assays, all primer designs showed unspecific amplification of chromosome 22. Upon further investigation, it was found that chromosome 22q11.2 cat eye syndrome region and chromosome 16 share 97% homology with exon 9 of the PIK3CA gene. To achieve gene specificity, primer and probe selectivity was maximized by strategically placing the exon 9 fluorescent probe and reverse primer over nucleotide sequence mismatch sites. The finalized exon 9 assay primer designs were Primer BLAST and found to generate a 100% matching sequence with chromosome 3; however, chromosome 22 was also detected with one mismatch in the 3' end of the reverse primer and one nucleic base shorter than the targeted sequence (see FIG. 9). The minus one base deviation of the unspecific chromosome 22 amplicon was the result of a deletion at nucleic acid position G1658. The exon 9 kPCR assay primers of the present invention in combination with thermal cycling stringency showed no evidence of pseudogene amplification.

FIG. 9 shows chromosome 3 and 22 sequence alignment. As shown therein, both the forward and reverse primer of exon 20 are in the exon region of the PIK3CA gene. The Primer BLAST result showed the primer designs are specific to PIK3CA gene only.

We claim:

1. A set of oligonucleotides for detecting KRAS gene mutations at one or more of codons 12, 13 and 61, comprising a forward primer, a reverse primer and a probe,
wherein the set of forward primer, reverse primer and probe is selected from the group consisting of sets of oligonucleotides with sequences consisting respectively of:
SEQ ID NO: 2, SEQ ID NO: 11, and SEQ ID NO: 10;
SEQ ID NO: 3, SEQ ID NO: 11, and SEQ ID NO: 10;
SEQ ID NO: 4, SEQ ID NO: 11, and SEQ ID NO: 10;
SEQ ID NO: 5, SEQ ID NO: 11, and SEQ ID NO: 10;
SEQ ID NO: 6, SEQ ID NO: 11, and SEQ ID NO: 10;
SEQ ID NO: 7, SEQ ID NO: 11, and SEQ ID NO: 10;
SEQ ID NO: 8, SEQ ID NO: 11, and SEQ ID NO: 10;
SEQ ID NO: 9, SEQ ID NO: 11, and SEQ ID NO: 10; and
SEQ ID NO: 24, SEQ ID NO: 25, and SEQ ID NO: 26.

2. The set of oligonucleotides of claim 1, wherein the sequences of the forward primer, reverse primer and probe consist of SEQ ID NO: 2, SEQ ID NO: 11, and SEQ ID NO: 10, respectively.

3. The set of oligonucleotides of claim 1, wherein the sequences of the forward primer, reverse primer and probe consist of SEQ ID NO: 3, SEQ ID NO: 11, and SEQ ID NO: 10, respectively.

4. The set of oligonucleotides of claim 1, wherein the sequences of the forward primer, reverse primer and probe consist of SEQ ID NO: 4, SEQ ID NO: 11, and SEQ ID NO: 10, respectively.

5. The set of oligonucleotides of claim 1, wherein the sequences of the forward primer, reverse primer and probe consist of SEQ ID NO: 5, SEQ ID NO: 11, and SEQ ID NO: 10, respectively.

6. The set of oligonucleotides of claim 1, wherein the sequences of the forward primer, reverse primer and probe consist of SEQ ID NO: 6, SEQ ID NO: 11, and SEQ ID NO: 10, respectively.

7. The set of oligonucleotides of claim 1, wherein the sequences of the forward primer, reverse primer and probe consist of SEQ ID NO: 7, SEQ ID NO: 11, and SEQ ID NO: 10, respectively.

8. The set of oligonucleotides of claim 1, wherein the sequences of the forward primer, reverse primer and probe consist of SEQ ID NO: 8, SEQ ID NO: 11, and SEQ ID NO: 10, respectively.

9. The set of oligonucleotides of claim 1, wherein the sequences of the forward primer, reverse primer and probe consist of SEQ ID NO: 9, SEQ ID NO: 11, and SEQ ID NO: 10, respectively.

10. The set of oligonucleotides of claim 1, wherein the sequences of the forward primer, reverse primer and probe consist of SEQ ID NO: 24, SEQ ID NO: 25, and SEQ ID NO: 26, respectively.

11. A kit for detecting KRAS mutations, comprising:
one or more sets of oligonucleotides of claim 1;
Taq polymerase; and
instructions for use.

* * * * *